(12) United States Patent
Sixto et al.

(10) Patent No.: US 8,685,068 B2
(45) Date of Patent: Apr. 1, 2014

(54) DISPOSABLE ORTHOPEDIC SURGERY KIT AND COMPONENTS

(75) Inventors: Robert Sixto, Miami, FL (US); Juergen Kortenbach, Miami Springs, FL (US); Jose L. Francese, Miami Springs, FL (US)

(73) Assignee: Biomet C.V., Gilbratar (GI)

( * ) Notice: Subject to any disclaimer, the term of this patent is extended or adjusted under 35 U.S.C. 154(b) by 66 days.

(21) Appl. No.: 12/884,242

(22) Filed: Sep. 17, 2010

(65) Prior Publication Data

US 2011/0071572 A1    Mar. 24, 2011

Related U.S. Application Data

(60) Provisional application No. 61/243,752, filed on Sep. 18, 2009.

(51) Int. Cl.
*A61B 17/80* (2006.01)
*A61B 17/84* (2006.01)
*A61B 17/58* (2006.01)
*A61B 19/02* (2006.01)

(52) U.S. Cl.
USPC ............. 606/286; 606/96; 606/915; 206/339; 206/363

(58) Field of Classification Search
USPC ............... 606/70–71, 104, 280–299, 915, 96; 206/339, 347, 363, 438
See application file for complete search history.

(56) References Cited

U.S. PATENT DOCUMENTS

| | | | |
|---|---|---|---|
| 3,716,050 A | 2/1973 | Johnston | |
| 3,770,119 A | 11/1973 | Hultberg et al. | |
| 4,596,329 A | 6/1986 | Eldridge, Jr. | |
| 5,040,676 A * | 8/1991 | Bell | 206/339 |
| 5,275,601 A | 1/1994 | Gogolewski et al. | |
| 5,569,247 A | 10/1996 | Morrison | |
| 5,601,553 A | 2/1997 | Trebing et al. | |
| 5,690,222 A | 11/1997 | Peters | |
| 5,690,489 A | 11/1997 | Carchidi | |
| 5,709,686 A | 1/1998 | Talos et al. | |
| 5,791,472 A | 8/1998 | Davis | |

(Continued)

FOREIGN PATENT DOCUMENTS

DE    20318732 U1    2/2004
EP    58219 B1    8/1982

(Continued)

OTHER PUBLICATIONS

International Search Report dated May 11, 2011; International Application No. PCT/US2010/049247.

(Continued)

*Primary Examiner* — Michael T Schaper
*Assistant Examiner* — Tracy Kamikawa
(74) *Attorney, Agent, or Firm* — Harness, Dickey

(57) ABSTRACT

A disposable single indication orthopedic trauma surgical kit has no bone plates other than a single bone plate precontoured and sized to match an anatomic shape of a portion of a bone of a patient's extremity. The single bone plate has a plurality of fastener apertures. The surgical kit also has a plurality of fasteners with heads that are dimensioned to mate with the fastener apertures. The surgical kit also has a disposable torque driver adapted to engage the fastener heads. The foregoing components are contained in a sterile sealed container.

16 Claims, 31 Drawing Sheets

(56) References Cited

U.S. PATENT DOCUMENTS

| | | | |
|---|---|---|---|
| 5,807,396 A | 9/1998 | Raveh | |
| 5,848,693 A | 12/1998 | Davis et al. | |
| 5,881,878 A * | 3/1999 | Faccioli et al. | 206/438 |
| 6,017,177 A | 1/2000 | Lanham | |
| 6,096,040 A | 8/2000 | Esser | |
| 6,161,695 A | 12/2000 | Nicolais | |
| 6,164,044 A | 12/2000 | Porfano et al. | |
| 6,189,292 B1 | 2/2001 | Odell et al. | |
| 6,250,052 B1 | 6/2001 | Porfano et al. | |
| 6,263,641 B1 | 7/2001 | Odell et al. | |
| 6,322,562 B1 | 11/2001 | Wolter | |
| 6,365,115 B1 | 4/2002 | Wood | |
| 6,426,041 B1 | 7/2002 | Smith | |
| 6,623,486 B1 | 9/2003 | Weaver et al. | |
| 6,730,091 B1 | 5/2004 | Pfefferle et al. | |
| 6,813,978 B1 | 11/2004 | Karpp | |
| 6,974,461 B1 | 12/2005 | Wolter | |
| 7,128,744 B2 | 10/2006 | Weaver et al. | |
| 7,179,260 B2 | 2/2007 | Gerlach et al. | |
| 7,350,643 B2 | 4/2008 | Capanni et al. | |
| 7,354,441 B2 | 4/2008 | Frigg | |
| 7,549,270 B2 | 6/2009 | Rowe et al. | |
| 2002/0045901 A1 | 4/2002 | Wagner et al. | |
| 2004/0167522 A1 | 8/2004 | Niederberger et al. | |
| 2004/0200754 A1 | 10/2004 | Hagemeier | |
| 2005/0015089 A1 | 1/2005 | Young et al. | |
| 2005/0033430 A1 * | 2/2005 | Powers et al. | 206/370 |
| 2005/0070904 A1 | 3/2005 | Gerlach et al. | |
| 2005/0137597 A1 | 6/2005 | Butler et al. | |
| 2005/0165400 A1 | 7/2005 | Fernandez | |
| 2005/0234472 A1 * | 10/2005 | Huebner | 606/104 |
| 2006/0122603 A1 | 6/2006 | Kolb | |
| 2006/0149250 A1 | 7/2006 | Castaneda et al. | |
| 2006/0231443 A1 | 10/2006 | Jonasson et al. | |
| 2006/0243616 A1 | 11/2006 | Caron | |
| 2006/0264946 A1 | 11/2006 | Young | |
| 2006/0266168 A1 | 11/2006 | Pacheco, Jr. | |
| 2007/0016205 A1 | 1/2007 | Beutter et al. | |
| 2007/0233114 A1 | 10/2007 | Bouman | |
| 2007/0260244 A1 | 11/2007 | Wolter | |
| 2008/0051786 A1 | 2/2008 | Jensen | |
| 2008/0091198 A1 | 4/2008 | Leibel et al. | |
| 2008/0116106 A1 | 5/2008 | Lampropoulos et al. | |
| 2008/0154281 A1 * | 6/2008 | Schaffran et al. | 606/104 |
| 2009/0171399 A1 | 7/2009 | White et al. | |
| 2009/0223851 A1 | 9/2009 | Jacobs et al. | |
| 2009/0254126 A1 | 10/2009 | Orbay et al. | |
| 2010/0140124 A1 | 6/2010 | Hafner | |
| 2010/0154353 A1 | 6/2010 | Cesa et al. | |

FOREIGN PATENT DOCUMENTS

| | | |
|---|---|---|
| EP | 207884 A2 | 1/1987 |
| EP | 1191890 B1 | 4/2002 |
| EP | 1474055 B1 | 11/2004 |
| EP | 1610700 B1 | 8/2010 |
| WO | WO 01/62136 A2 | 8/2001 |
| WO | WO 0154601 A1 | 8/2001 |
| WO | WO 02096309 A1 | 12/2002 |
| WO | WO 2009102985 A2 | 8/2009 |

OTHER PUBLICATIONS

Catalog 0612-24-508 "A.L.P.S. Anatomic Locking Plate System", © 2009, DePuy Orthopaedics, Inc., 700 Orthopaedic Dr., Warsaw, IN 46581-0988, USA.

Co-owned and co-pending U.S. Appl. No. 12/884,246.

* cited by examiner

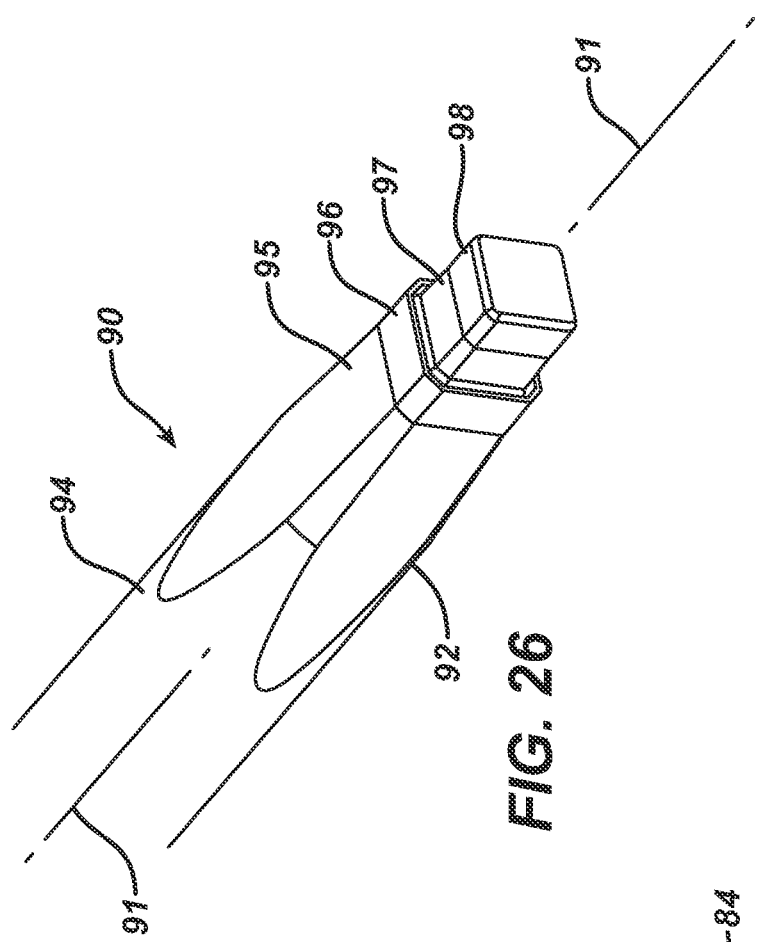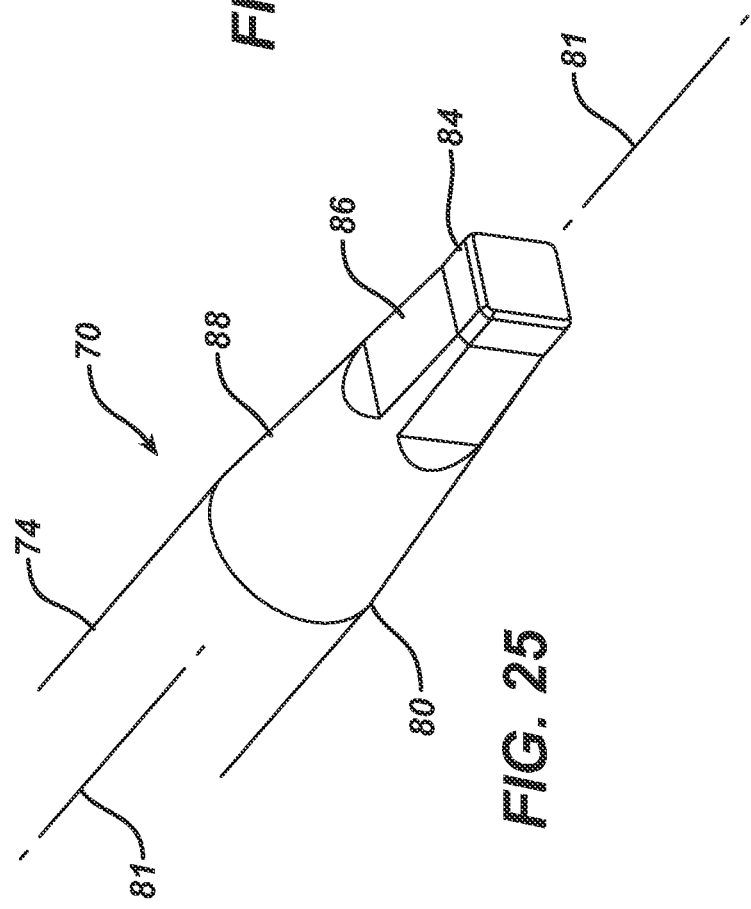

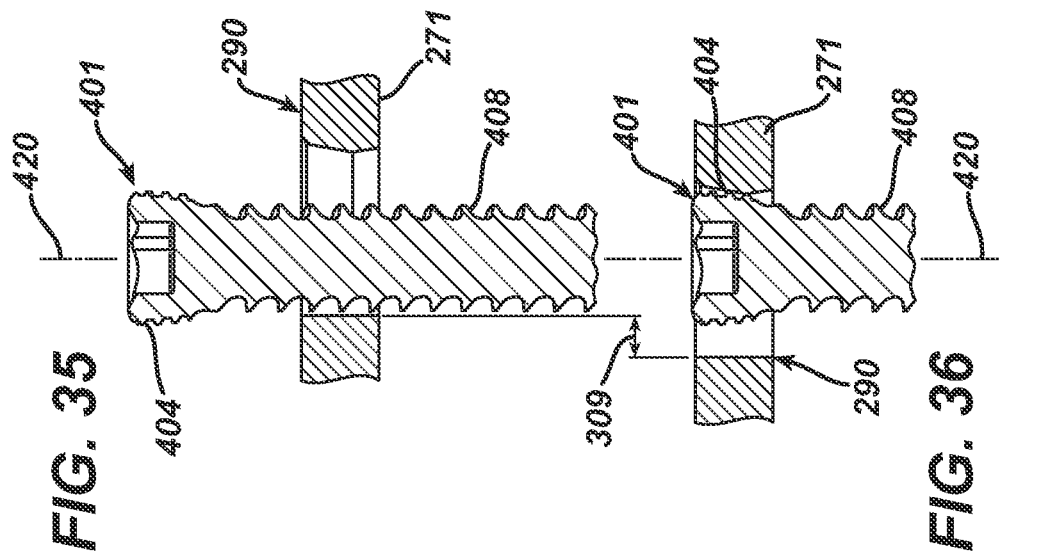
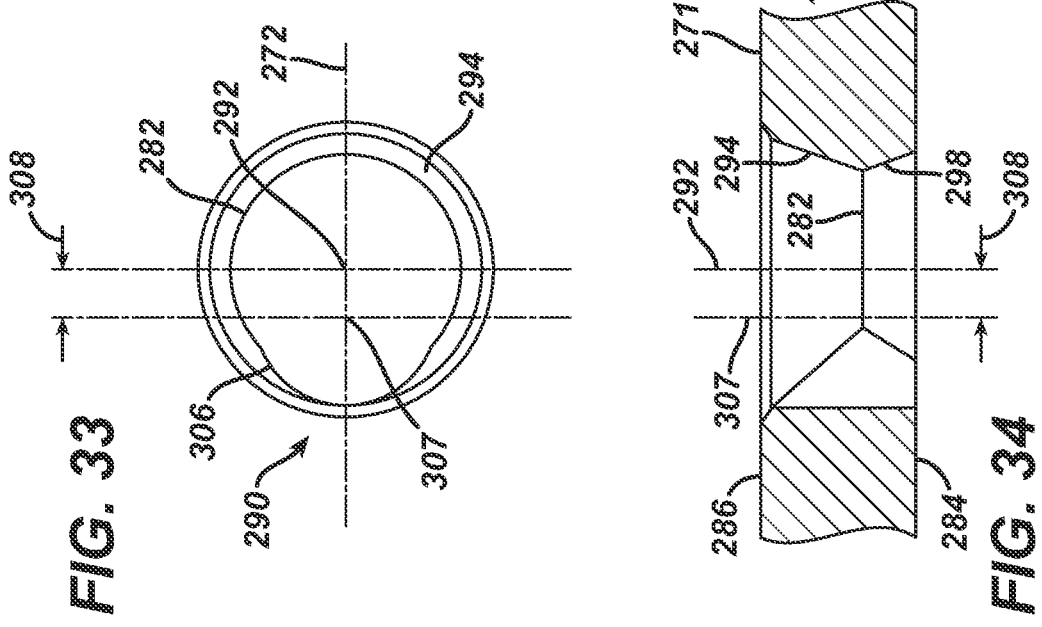

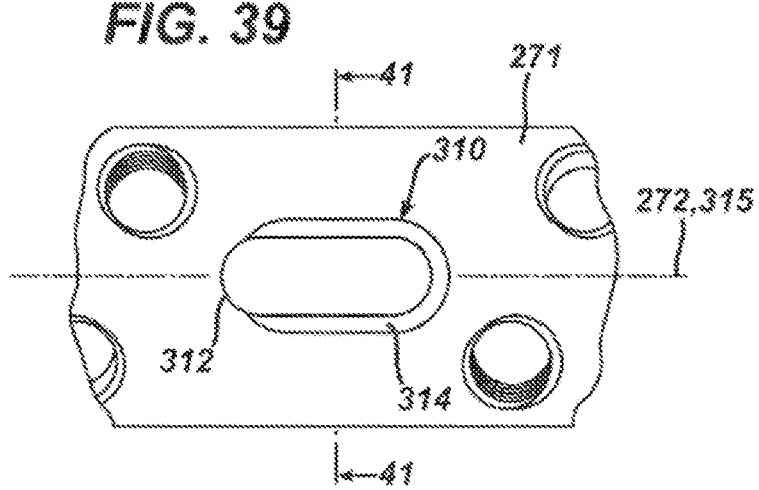
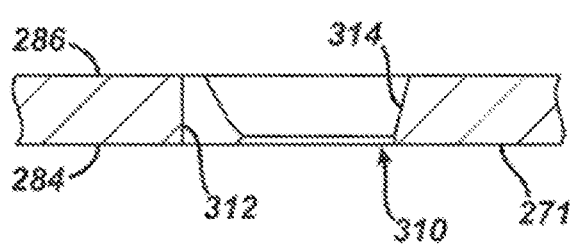
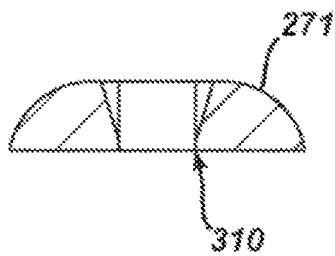

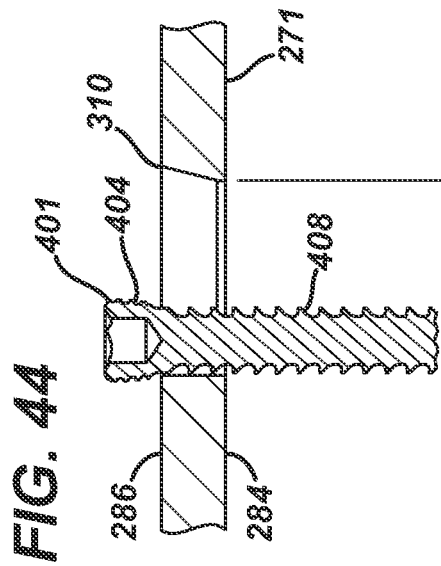
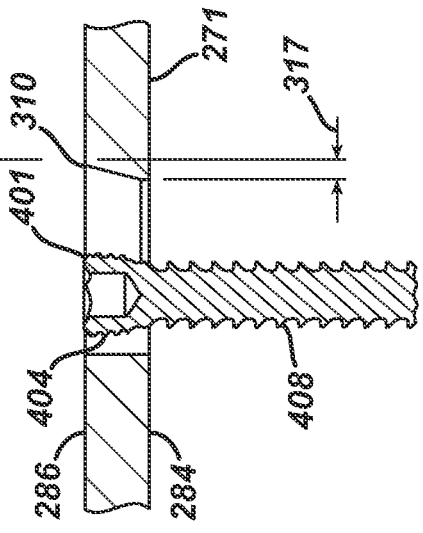
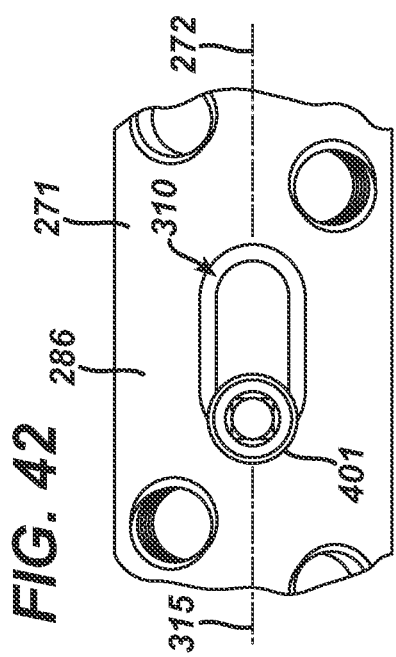
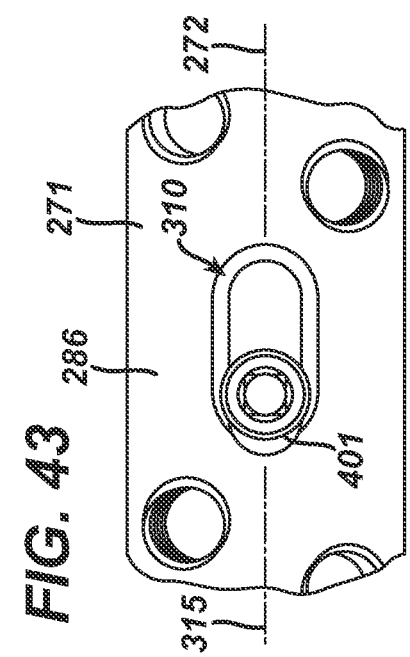

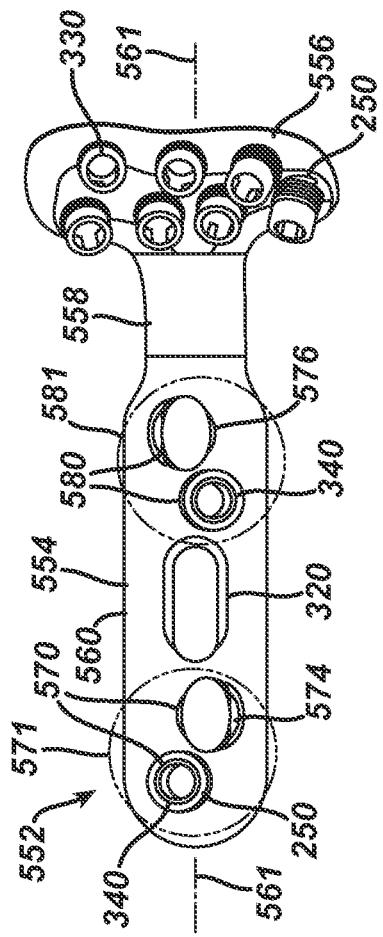
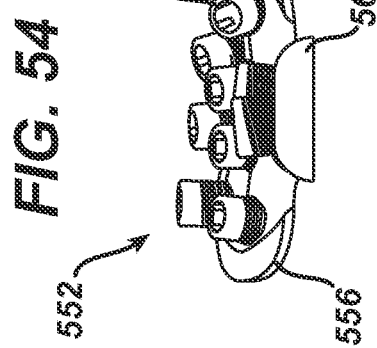
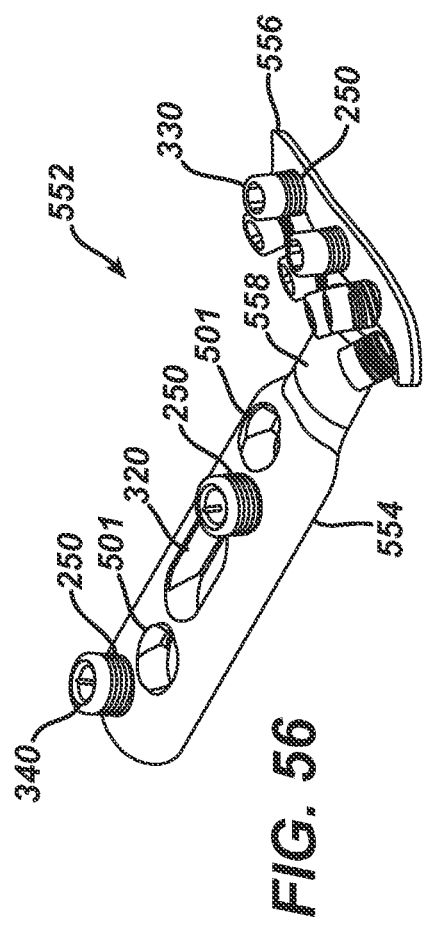

DISPOSABLE ORTHOPEDIC SURGERY KIT AND COMPONENTS

RELATED APPLICATIONS

This application claims the benefit of provisional U.S. patent application no. 61/243,752 filed on Sep. 18, 2009.

BACKGROUND

This disclosure relates generally to surgical devices and procedures, and more particularly, to orthopedic surgical devices and procedures for the internal fixation of fractured bones.

Bone plate systems for the internal fixation of fractured bones of patients are typically provided by manufacturers in non-sterile, reusable trays to the surgical care facilities. These trays may include a number of bone plates of various types, sizes and shapes for various patient anatomies and surgical indications. The trays also may include a number of reusable instruments and a large number of bone plate fasteners of numerous sizes and types, many more than what would normally be required for any given patient and surgical indication. Prior to the surgical procedure, the surgical care facility personnel must be sure that a complete tray of these components is assembled and sterilized, such as by steam autoclave. Often a manufacturer's sales representative may be present at the facility to assist in assembling the tray of necessary components in preparation for the surgical procedure. After the procedure is completed, the tray of unused components may be sterilized and stored for a later surgical procedure. Any components missing from the tray generally are replenished and the entire tray is sterilized again prior to a surgical procedure for another patient.

The overall cost of providing to the surgeon many more components in sterile condition than would normally be required for a particular patient with a specific surgical indication can be significant. This overall cost may include costs related to the necessary inventory of bone plate system components, repeated sterilization of the components, the need to make high quality, durable instruments for repeated use, the assistance of manufacturers' representatives, and other factors. Such factors may also impact the availability of such bone plate systems to trauma surgeons practicing in certain areas of the world.

SUMMARY

A disposable single indication orthopedic trauma surgical kit has no bone plates other than a single bone plate precontoured and sized to match an anatomic shape of a portion of a bone of a patient's extremity. The single bone plate has a plurality of fastener apertures. The kit also has a plurality of fasteners, each comprising a head and a shaft. The heads are dimensioned to mate with the fastener apertures. The kit also has a disposable torque driver adapted to engage the fastener heads. The foregoing components are contained in a sterile sealed container.

The portion of the bone may be any one of the right distal volar radius, the left distal volar radius, the right fibula, the left fibula, the right proximal radius, the left proximal radius, the right navicular, the left navicular, the right distal ulna, and the left distal ulna. All of the fasteners in the surgical kit may have the same sized head, while all of the fastener apertures of the single bone plate may be dimensioned to receive the same sized head. All of the fasteners in the surgical kit may have only one of two different sized heads. Alternatively, all of the fasteners in the surgical kit may have either a first sized head or a second sized head, while all of the fastener apertures of the single bone plate may be dimensioned to receive either the first sized head or the second sized head. The surgical kit may include thirty-six or fewer fasteners, each of which may have only one of nine or fewer different shaft lengths. The fasteners may be arranged in the container in a plurality of groupings of four or fewer fasteners, each having the same shaft length. The container may include labels to indicate the shaft length of each of the plurality of groupings of fasteners. The container may include a plurality of fastener length gages to aid the user in determining the length of each of the plurality of fasteners. The surgical kit may also include a wire drill, a drill guide, and a depth gage, all contained in the sterile sealed container. In addition, the surgical kit may be resterilizable by a steam autoclave once the sterile sealed kit has been opened.

A disposable single indication orthopedic trauma surgical kit includes a single bone plate adapted for a use on a bone of a patient's extremity. The bone plate has a plurality of fastener holes. The kit also has a plurality of fasteners, each comprising a head and a shaft. The heads are adapted to interface with the fastener holes. The kit also includes a disposable torque driver adapted to engage the fastener heads, one or more wire drills, one or more drill guides, and a disposable depth gage. All of the foregoing components are contained in a sterile sealed container.

A system of single indication orthopedic trauma surgical kits includes a sterile sealed left DVR kit for treatment of fractures of the left distal volar radius. The left DVR kit includes a sterile sealed container, a single bone plate that is anatomically shaped and sized to match the left distal volar radius, a plurality of fasteners, a fastener driver, a wire drill, a drill guide, and a depth gage. The system also includes a sterile sealed right DVR kit for treatment of fractures of the right distal volar radius. The right DVR kit includes a sterile sealed container, a single bone plate that is anatomically shaped to match the right distal volar radius, a plurality of fasteners, a fastener driver, a wire drill, a drill guide, and a depth gage. The system also includes a sterile sealed fibula kit for treatment of fractures of the fibula. The fibula kit includes a sterile sealed container, a single bone plate that is anatomically shaped to match the right and left fibula, a plurality of fasteners, a fastener driver, a wire drill, a drill guide, and a depth gage. The system also includes a sterile sealed distal ulna kit for treatment of fractures of the distal ulna. The distal ulna kit includes a sterile sealed container, a single bone plate that is anatomically shaped to match the right and left distal ulna, a plurality of fasteners, a fastener driver, a wire drill, a drill guide, and a depth gage.

Each of the sterile sealed kits of the system may be steam autoclave resterilizable after the kit has been opened. The containers of all the sterile sealed kits may have a common design that is configurable for different surgical indications. Each kit may include displayed graphics that pertain to the surgical indication and use of the kit. Each kit may have one of a number of colors, each color corresponding to one of a number of surgical indications.

A bone plate system for the internal fixation of a fractured bone of a patient has a bone plate with a bone-facing bottom surface, an opposing top surface, and a thickness between the surfaces. The bone plate also has one or more threaded bone fastener apertures and one or more non-threaded bone fastener apertures. The bone plate system further has a plurality of bone fasteners, each fastener comprising a shaft and a head. The heads are dimensioned and configured to threadedly engage the threaded bone fastener apertures to provide a fixed angle locking construct. The heads are also dimensioned and configured to directly engage the non-threaded bone fastener apertures to provide a polyaxial non-locking compressive construct.

At least one of the non-threaded bone fastener apertures may be a unidirectionally ramped aperture for dynamic compression of the fractured bone in one direction. The at least one unidirectionally ramped aperture may be an elongated slot. Also, the threaded and non-threaded bone fastener apertures of the bone plate may have the same nominal size. At least some of the plurality of bone fasteners may be threaded for engagement into bone and at least some of the plurality of bone fasteners may have non-threaded, smooth shafts. The head of each bone fastener may have a tapered external screw thread that has a flat helical crest defining a frustoconical shape. The tapered external screw thread may have either one of a double lead type of thread and a triple lead type of thread. The tapered external screw thread may have a pitch distance between adjacent threads of about 0.500 to 0.600 millimeters. Furthermore, the flat helical crest may have a width in the range of about 0.120 to 0.160 millimeters and the ratio of the width of the flat helical crest to the pitch distance between threads may be about 0.200 to 0.320. The bone plate may be sized and shaped for the internal fixation of a fractured bone of a human extremity. The bone plate may also include a shaft portion having a plurality of regions, each region having one of the non-threaded bone fastener apertures and one of the threaded bone fastener apertures paired together. A surgeon may attach the bone plate to approximately the same part of the bone by selecting one of the threaded and non-threaded bone fastener apertures in any one of the regions and inserting one of the bone fasteners into the selected aperture.

A bone plate system for the internal fixation of a fractured bone of a patient has a bone plate with a bone facing bottom surface, an opposing top surface, and a thickness between the surfaces. The bone plate also has a plurality of bone fastener apertures of a first size. The plurality of bone fastener apertures have one or more apertures of a first type having a tapered threaded surface and one or more apertures of a second type having a tapered smooth surface. The bone plate system also has a plurality of bone fasteners, each comprising a shaft and a head of a first size. The heads are dimensioned and configured to threadedly engage the first type of bone fastener aperture to provide a fixed angle locking construct. The heads are also dimensioned and configured to directly engage the second type of fastener aperture to provide a polyaxial non-locking compressive construct.

The bone plate may have only bone fastener apertures of the first size and may also have one or more non-fastener apertures.

A bone plate system has a bone plate with a bone facing bottom surface, an opposing top surface, and a thickness between the surfaces. The bone plate further has a plurality of bone fastener apertures of a first size and a plurality of bone fastener apertures of a second size. The first and second sized apertures each have one or more apertures of a first type having a tapered surface with internal threads and one or more apertures of a second type having a tapered smooth surface. The bone plate system also has a plurality of first bone fasteners, each comprising a shaft and a head of a first size. The heads are dimensioned and configured to threadedly engage the first type of apertures of the first size to provide a fixed angle locking construct. The heads also are dimensioned and configured to directly engage the second type apertures of the first size to provide a polyaxial non-locking compressive construct. The bone plate system also has a plurality of second bone fasteners, each comprising a shaft and a head of a second size. The heads are dimensioned and configured to threadedly engage the first type of apertures of the second size to provide a fixed angle locking construct. The heads are also dimensioned and configured to directly engage the second type of apertures of the second size to provide a polyaxial non-locking compressive construct.

The bone fastener apertures of the first and second sizes of the second type may have at least one unidirectionally ramped aperture for dynamically compressing the fractured bone in one direction. The bone fastener apertures of the first and second sizes of the second type may include at least one bidirectionally ramped aperture for dynamically compressing the fracture bone in either one of two opposing directions. The head of the first bone fastener may have a first drive socket and the head of the second bone fastener may include a second drive socket, and the first and second drive sockets may be dimensioned to receive a driver tip of a torque driver for insertion of the first and second bone fasteners into bone. Furthermore, the first drive socket may have a first configuration. The second drive socket may have a stepped recess with a distal recess having the first configuration and a coaxial, adjacent proximal recess with a second configuration. The second configuration may be larger than the first configuration as viewed along the axis. Either one or both of the distal and proximal recesses can transmit a torque from the torque driver to the head of the second bone fastener.

BRIEF DESCRIPTION OF FIGURES

While this specification concludes with claims that particularly point out and distinctly claim the invention, the following description and the accompanying figures further illustrate some non-limiting examples of the claimed invention. Unless otherwise indicated, like reference numerals identify the same elements.

FIG. 25 is a perspective, detail view of the first drive tip shown in FIG. 14;

FIG. 26 is a perspective, detail view of a second drive tip;

FIG. 33 is a top view of a unidirectionally ramped aperture;

FIG. 34 is a cross-sectional view of the unidirectionally ramped aperture of FIG. 33;

FIG. 35 is a cross-sectional view of the unidirectionally ramped aperture of FIG. 34 with the first fastener of FIG. 20 partially inserted therein;

FIG. 36 is a cross-sectional view of the unidirectionally ramped aperture of FIG. 35 with the first fastener of FIG. 20 fully inserted therein;

FIG. 39 is a top view of a unidirectionally ramped slot positioned along a longitudinal axis of a plate;

FIG. 40 is a cross-sectional view taken through the longitudinal axis of the plate of FIG. 39, showing a unidirectionally ramped slot;

FIG. 41 is a cross-sectional view taken through line 41-41 of FIG. 39, showing the unidirectionally ramped slot of FIG. 39;

FIG. 42 is a top view of the first fastener partially inserted into the unidirectionally ramped slot of the bone plate;

FIG. 43 is a top view of the first fastener fully inserted into the unidirectionally ramped slot;

FIG. 44 is a cross-sectional view, taken through the longitudinal axis, of the first fastener partially inserted into the unidirectionally ramped slot as shown in FIG. 42;

FIG. 45 is a cross-sectional view, taken through the longitudinal axis, of the first fastener fully inserted into the unidirectionally ramped slot as shown in FIG. 43;

FIG. 54 is an end view of a third DVR assembly;

FIG. 55 is a top view of the third DVR assembly of FIG. 54; and

FIG. 56 is a perspective view of the third DVR assembly of FIG. 54.

DETAILED DESCRIPTION

Figure 1:
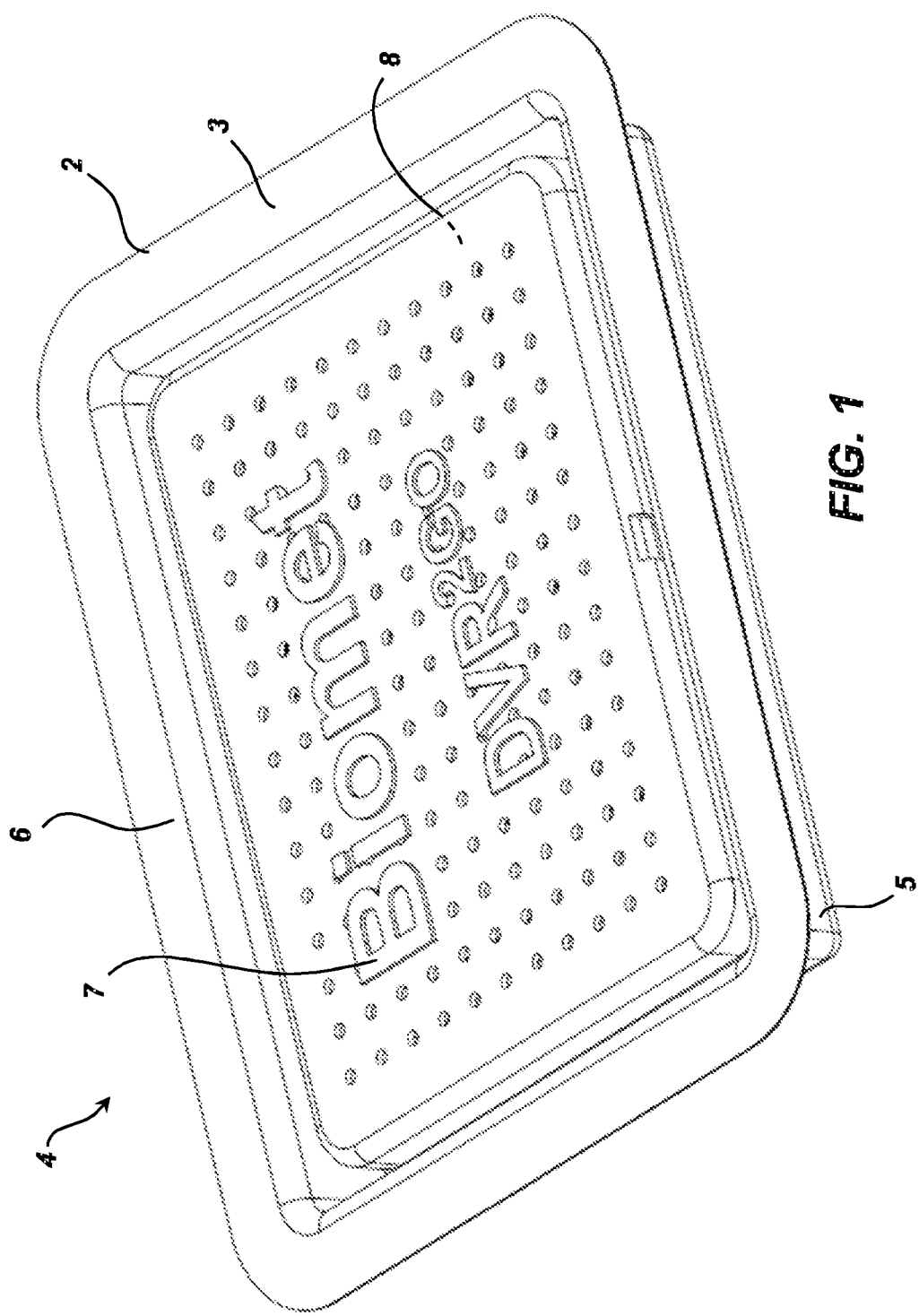
FIG. 1 is a top perspective view of a single-use, orthopedic surgery kit (or more simply, a single-use kit), showing a first embodiment of a container sealed inside of an outer package.

Throughout the following description, the term "user" may refer to the surgeon or other users of the single-use kit, including surgical assistants, technicians, and so on. Also, the term "single-use", as used herein, is interchangeable with the terms "disposable" or "disposable, single-indication", meaning that the kit, including all the components contained therein, is intended for use for only one surgical patient. After completion of the surgical procedure, the components that are not implanted into the patient may be discarded using conventional methods. However, for some embodiments, it is also possible that the single-use kit or a portion of it can be resterilized for use in a surgical procedure for another patient.

Each single-use kit is designed for transport from the manufacturer to the surgical care facility, storage, and then finally, sterile presentation to the surgeon for use during the surgical procedure. Using the appropriate single-use kit for a particular surgical procedure may reduce the need for the surgical care facility to maintain a large inventory of individual components that must be combined into a surgical tray and sterilized prior to that procedure. Furthermore, using the appropriate single-use kit may reduce the need for special assistance from the representatives of the component manufacturers, and assures the surgeon that the components are always new and in sterile condition. In addition, since the single-use kit may be designated to have a single product code, expensing the cost of the kit to the patient and/or the patient's health care provider may be simplified and result in reduced overhead costs for the surgical procedure.

We envision that occasionally the surgeon may select a single-use kit containing components for a particular type of bone fracture procedure, and then determine during the surgical procedure that the single-use kit is not appropriate for that patient. In case a single-use kit is contaminated during (or prior to) a surgical procedure for a patient and then is not used for that patient, it is possible to steam autoclave the kit with the components contained therein, such that the kit may be used in a surgical procedure for a different patient.

One advantage of these single-use kit embodiments is the commonality of components that is possible due to the reduction of the number of bone plate fastener types required, as compared to currently available systems for similar surgical procedures. By minimizing the variety of required fastener types for attaching a plurality of different types of bone plates, an economy is realized in the instrumentation required to perform the various surgical procedures. As a consequence, the size and cost of the single-use kit is minimized. We envision that this may increase availability of such kits to surgical care centers throughout the world, so that more trauma patients may be treated using the latest implants, instruments and techniques. In addition, we envision that the overall surgical procedure may be simplified, potentially resulting in reduced surgical procedure duration and improved clinical outcome for the patient.

Referring now to the figures, FIG. 1 is a top perspective view of a single-use kit 4, which includes a container 8 according to a first embodiment, a plurality of components (not visible) contained therein, and an outer package 2. (Each of the plurality of components will be later described in detail for each of the single-use kit embodiments disclosed herein.) Outer package 2 physically protects container 8 and the components contained therein, and may also serve to seal and to maintain the sterility of container 8 and the components contained therein until accessed prior to or during the surgical procedure.

Outer package 2 may be formed from materials and by methods that are well known in the art for the sterile packaging of medical devices. Outer package 2 includes a pan 5 that is sized and shaped to hold container 8. Pan 5 has a peripheral lip 3 and may be formed from a plastic material suitable for maintaining sterility. Outer package 2 may include a removably attachable, sealing membrane 6 that is adhered to peripheral lip 3 of pan 5 prior to sterilization by gamma radiation or other sterilization methods known in the art. The user peels sealing membrane 6 from pan 5 to access container 8. Sealing membrane 6 may be formed from a suitable, transparent plastic material so that a graphic 20 displayed on container 8 is visible prior to opening outer package 2. Graphic 20 may provide information pertaining to, for example, the manufacturer, the distributor, the surgical indications, the product code(s), the components contained therein, the overall physical characteristics (i.e., size and weight), the relevant patents, warnings, directions for opening, and so on. Alternatively, sealing membrane 6 may be formed from a suitable, solidly colored or translucent plastic material, and may include a graphic that is similar or complementary to graphic 20.

It should be understood that other embodiments of single-use kit 4 may not include outer package 2 at all or that outer package 2 may provide only non-sterile protection for container 8 and the components contained therein. For example, container 8 and the components contained therein may be first removed from outer package 2 in a non-sterile condition and then sterilized at the surgical care facility prior to the surgical procedure.

Figure 2:
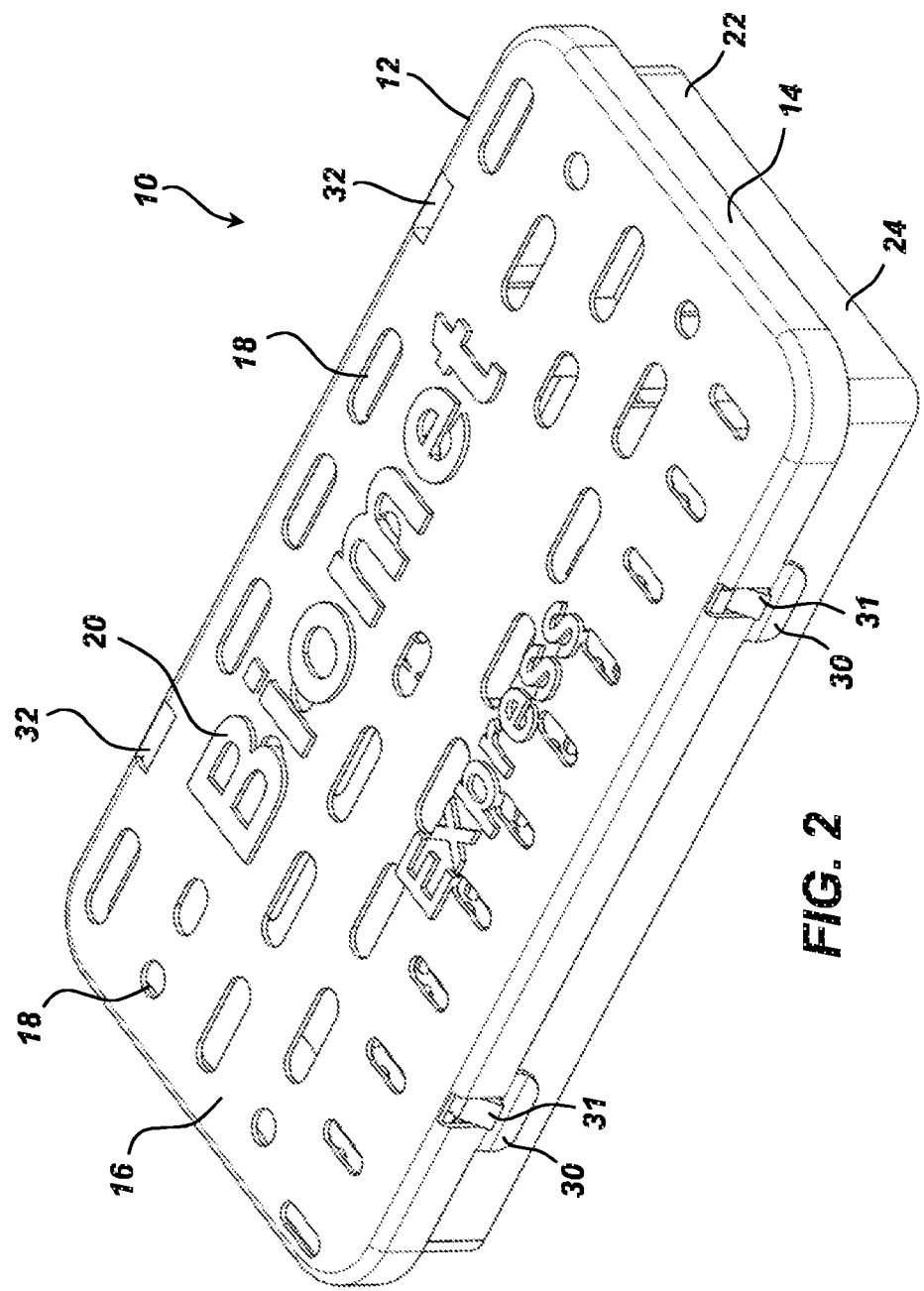
FIG. 2 is a top perspective view of an alternative embodiment of a container, which includes a bottom tray and a top lid, shown with the lid closed.
Figure 3:
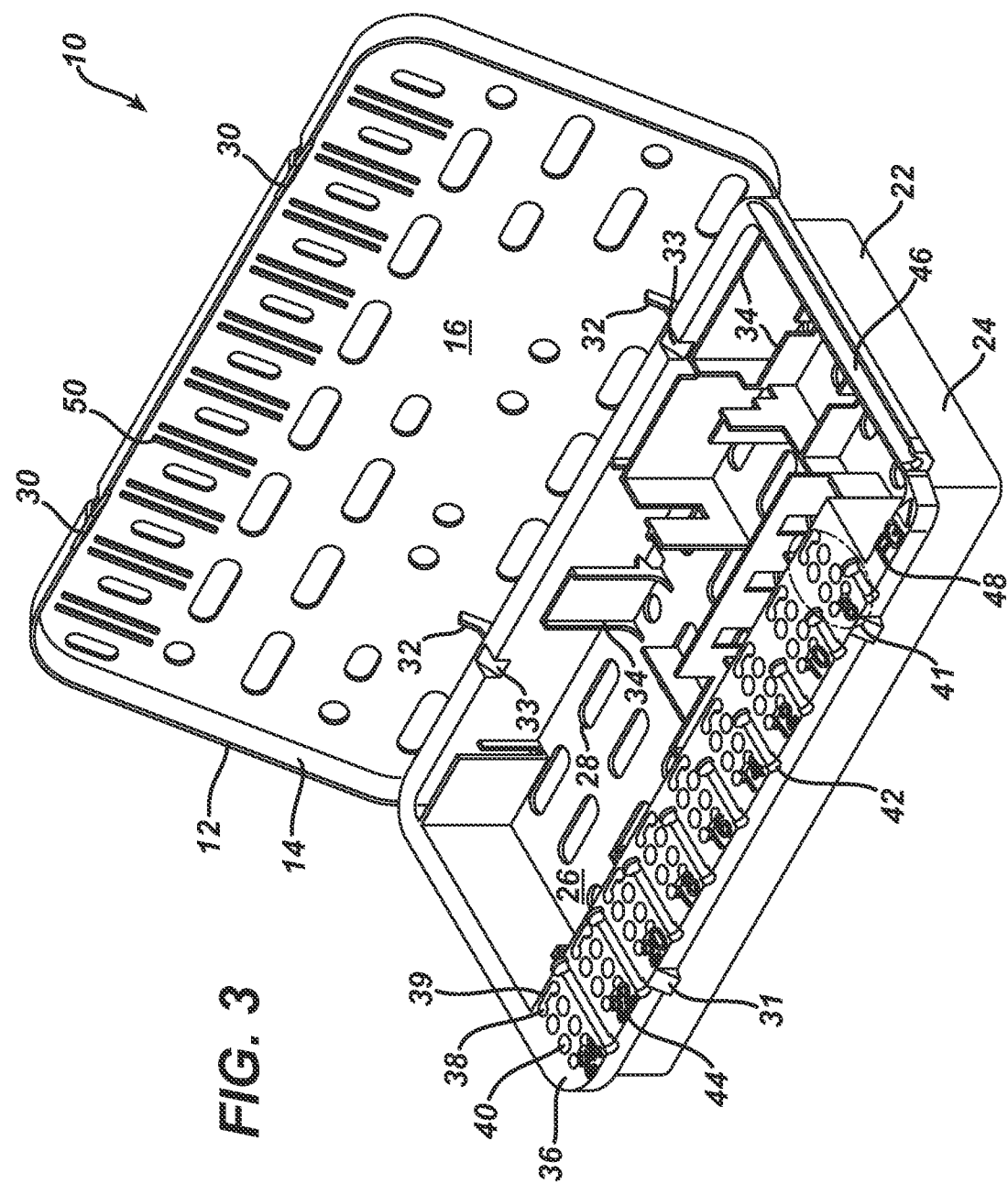
FIG. 3 is a top perspective view of the container of FIG. 2, shown with the lid opened.

FIG. 2 is a top perspective view of a container 10 in a closed configuration according to a second embodiment. FIG. 3 is a top perspective view of container 10 in an open configuration. Container 10 includes a bottom tray 22 and a top lid 12, each of which is formed, such as by injection molding, from any one of a number of polymers, including, for example, polysulfone, polyetherimide and polypropylene. Either one or both of tray 22 and lid 12 may be formed from a transparent polymer to allow viewing of the components contained therein without opening container 10.

Lid 12 may be formed from a polymer that is colored to indicate the surgical indication of the kit or to provide some other type of information to the user. For example, a red color may indicate that the kit is to be used for the right side of the patient's anatomy, a lime color may indicate that the kit is to be used for the left side, and a white color may indicate that the kit is to be used for either side.

As shown in FIGS. 2 and 3, tray 22 has a rectangular shape defined by four tray sides 24, although other shapes may be desirable depending on functional, economic, aesthetic or other reasons. Tray 22 includes a tray bottom 26 that includes a plurality of openings 28 to facility steam access and drainage during sterilization. Lid 12 has a top portion 16 and a peripheral lip 14 that is sized and shaped to fit closely around tray 22. Top portion 16 of lid 12 includes a plurality of openings 18 to facilitate steam sterilization and drainage of container 10 and the components contained therein. Graphic 20 may be integrally molded into top portion 16 of lid 12 and/or selectively highlighted with a suitable ink or paint, such as is well known in the art.

A pair of spaced apart, lid hinge elements 32 is integrally formed on lid 12 for attachment to a pair of spaced apart, tray hinge elements 33 integrally formed on tray 22. Lid 12 may be removably attachable to tray 22 to facilitate access to the components in tray 22 during the surgical procedure, while conserving available space on the surgical stand.

Similarly, a pair of spaced apart, lid latch elements 30, positioned on the opposite side from lid hinge elements 32 of container 10, is integrally formed on lid 12 for attachment to a pair of spaced apart, tray latch elements 31 formed on tray 22. As is well known in the art, many types of lid hinge elements 32, lid latch elements 30, tray hinge elements 33 and tray latch elements 31 are possible.

Figure 4:
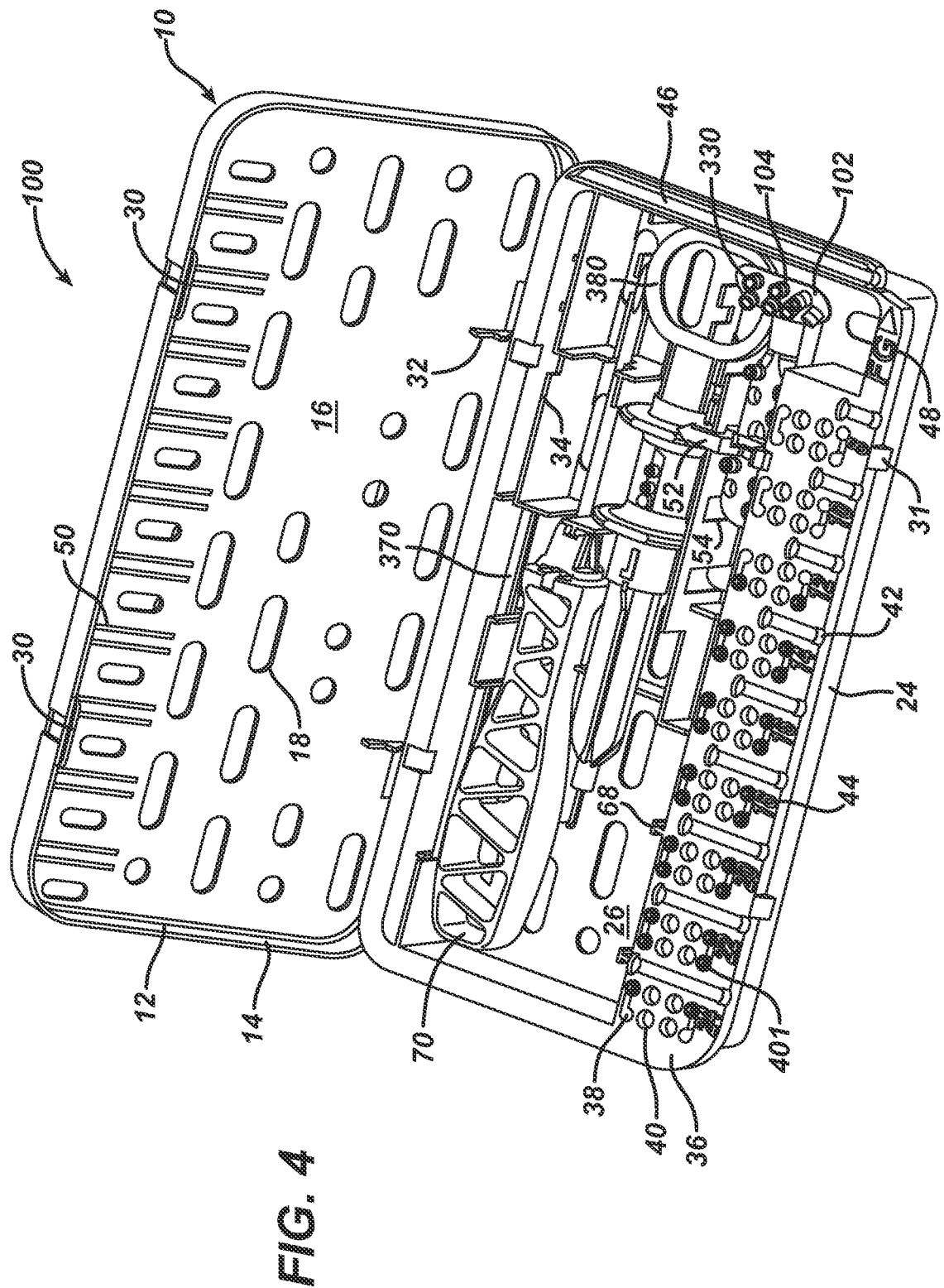
FIG. 4 is a top perspective view of a single-use, distal volar radius (or DVR) kit.

As shown in FIG. 4, tray 22 is compartmentalized by several, integrally formed partitions 34 extending from the inside of tray bottom 26 and the inside of tray sides 24. Tray 22 also includes a shelf 36 that serves as an easily accessible, "screw caddy" for holding a plurality of implantable fasteners, including, for example, a plurality of first fasteners 401 and a plurality of second fasteners 451 (as shown, for example, in FIG. 8). Shelf 36 and partitions 34 are configured to organize and retain the various combinations of all the required components for at least each of the embodiments, as will be described, of the single-use kit embodiments shown herein.

Figure 8:
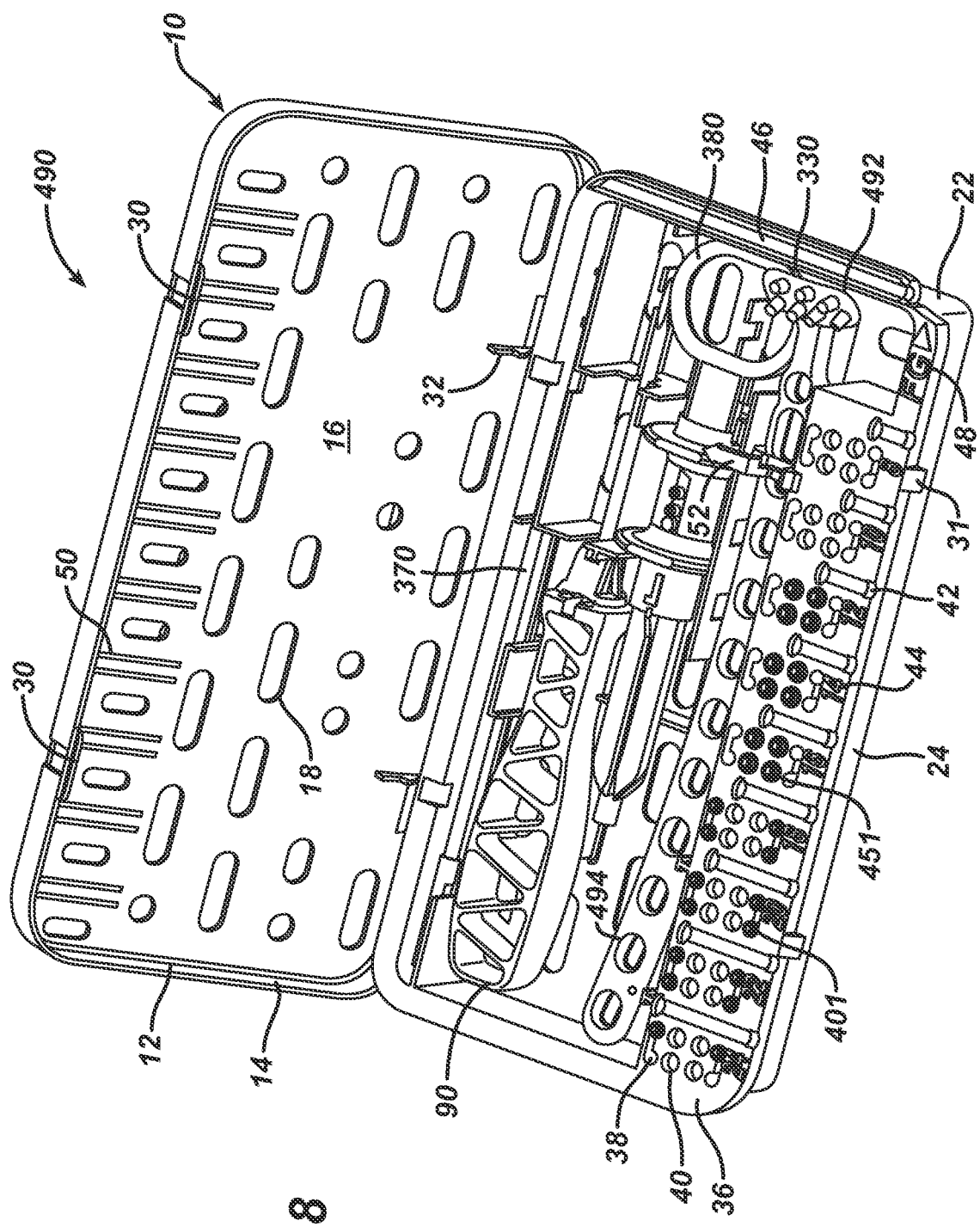
FIG. 8 is a top perspective view of a single-use, DVR long kit.
Figure 9:
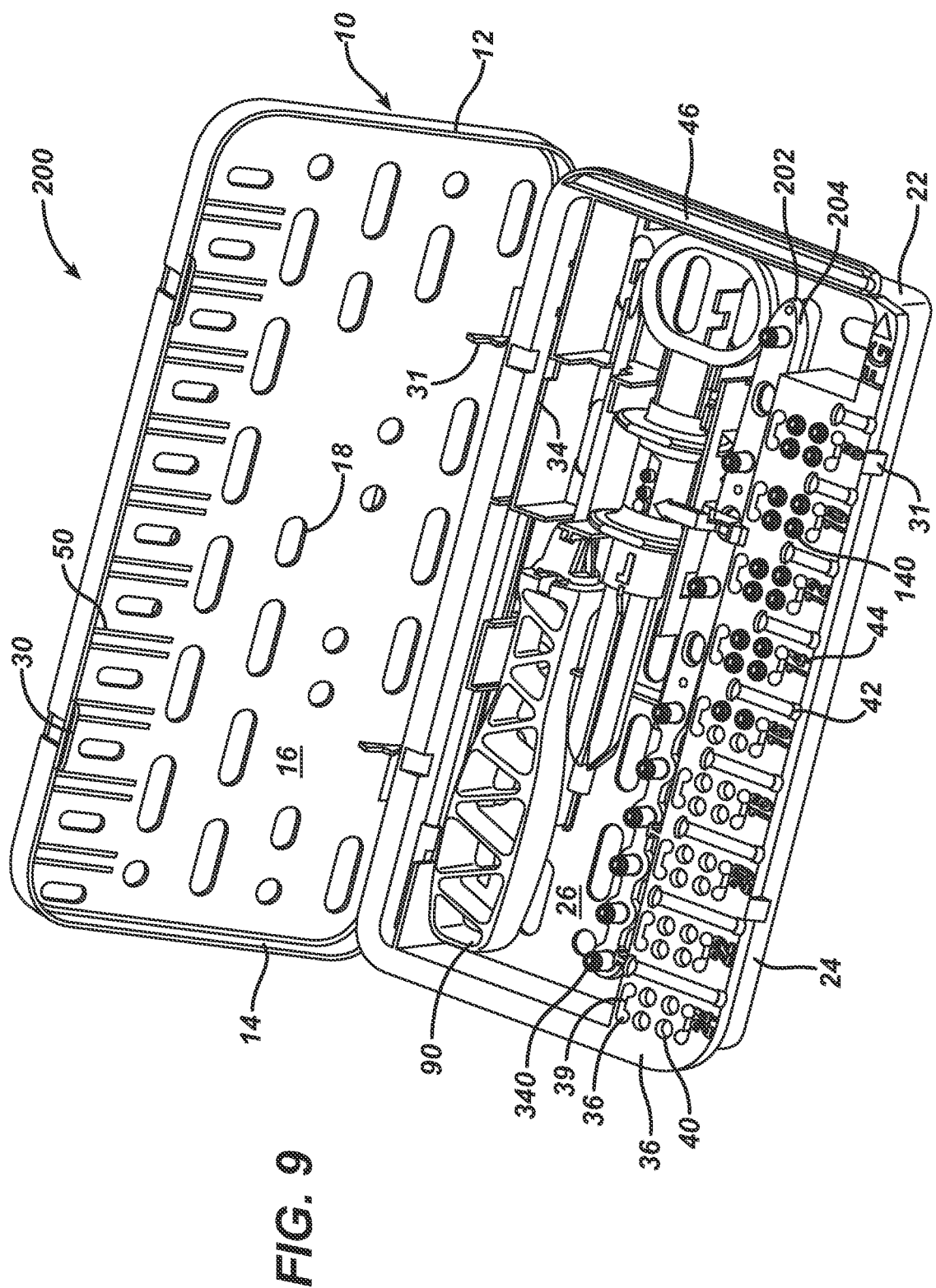
FIG. 9 is a top perspective view of a single-use, fibula kit.
Figure 10:
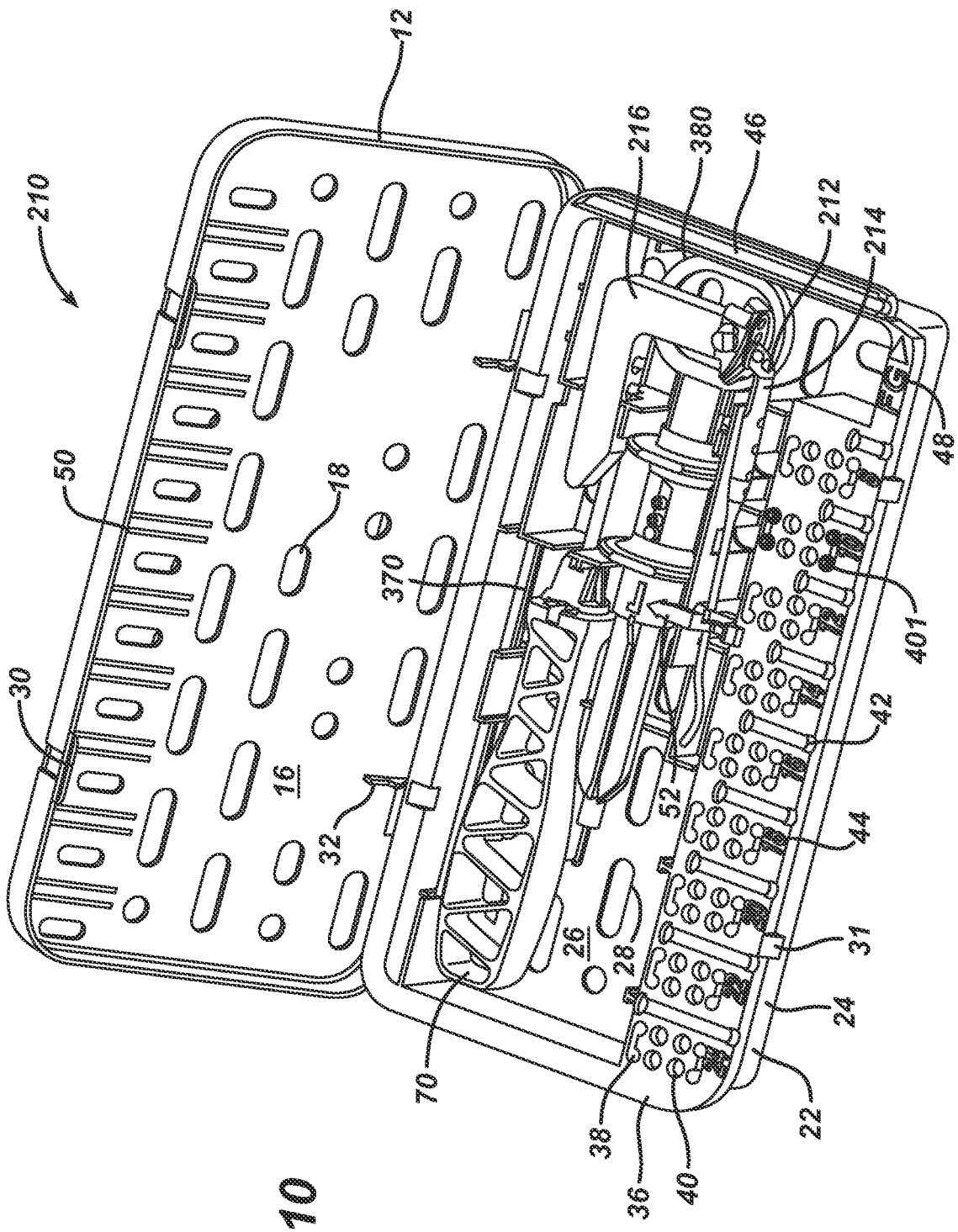
FIG. 10 is a top perspective view of a single-use, dorsal nail plate (or DNP) kit.
Figure 11:
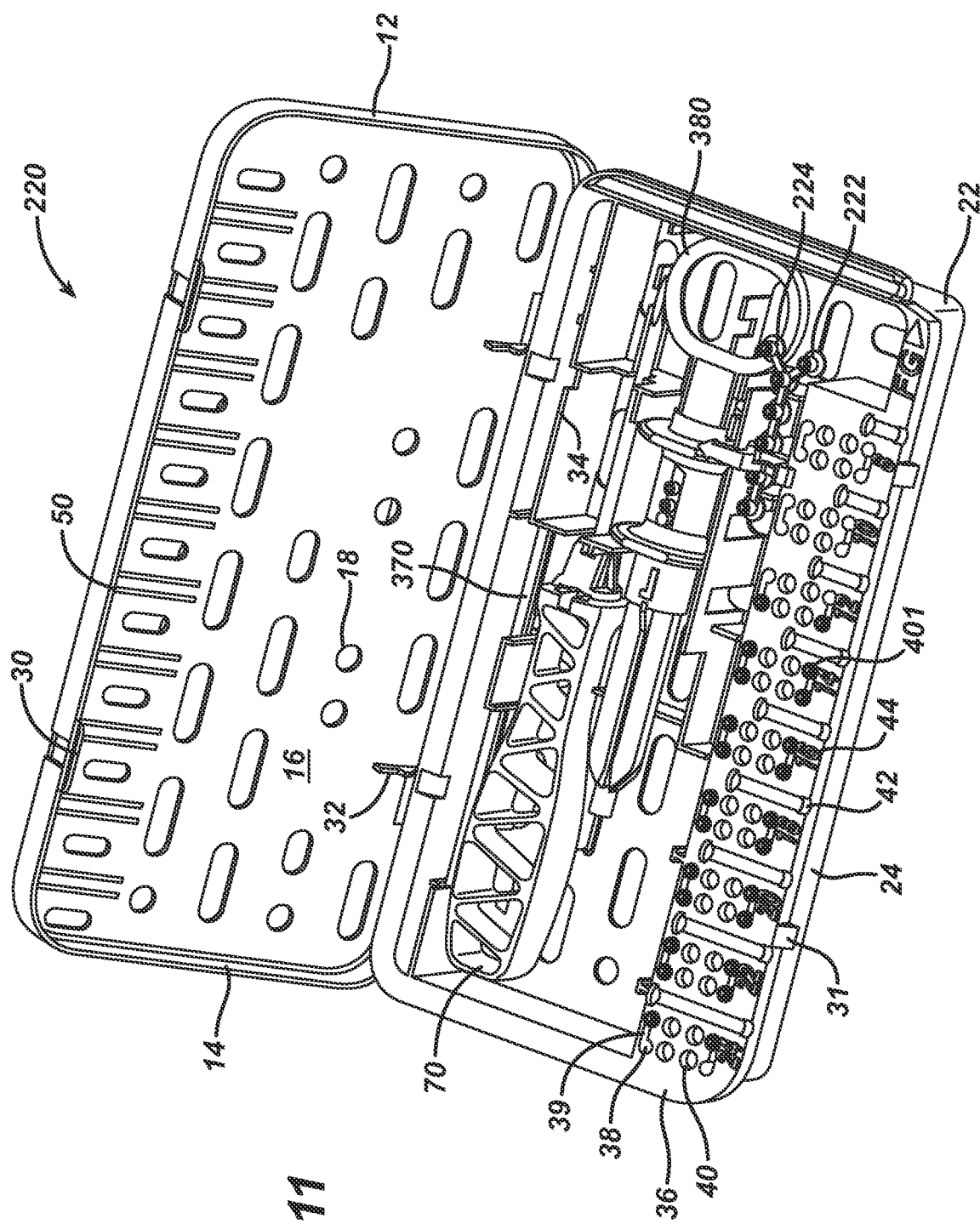
FIG. 11 is a top perspective view of a single-use, flexible fragment fixation (or F3) kit.
Figure 12:
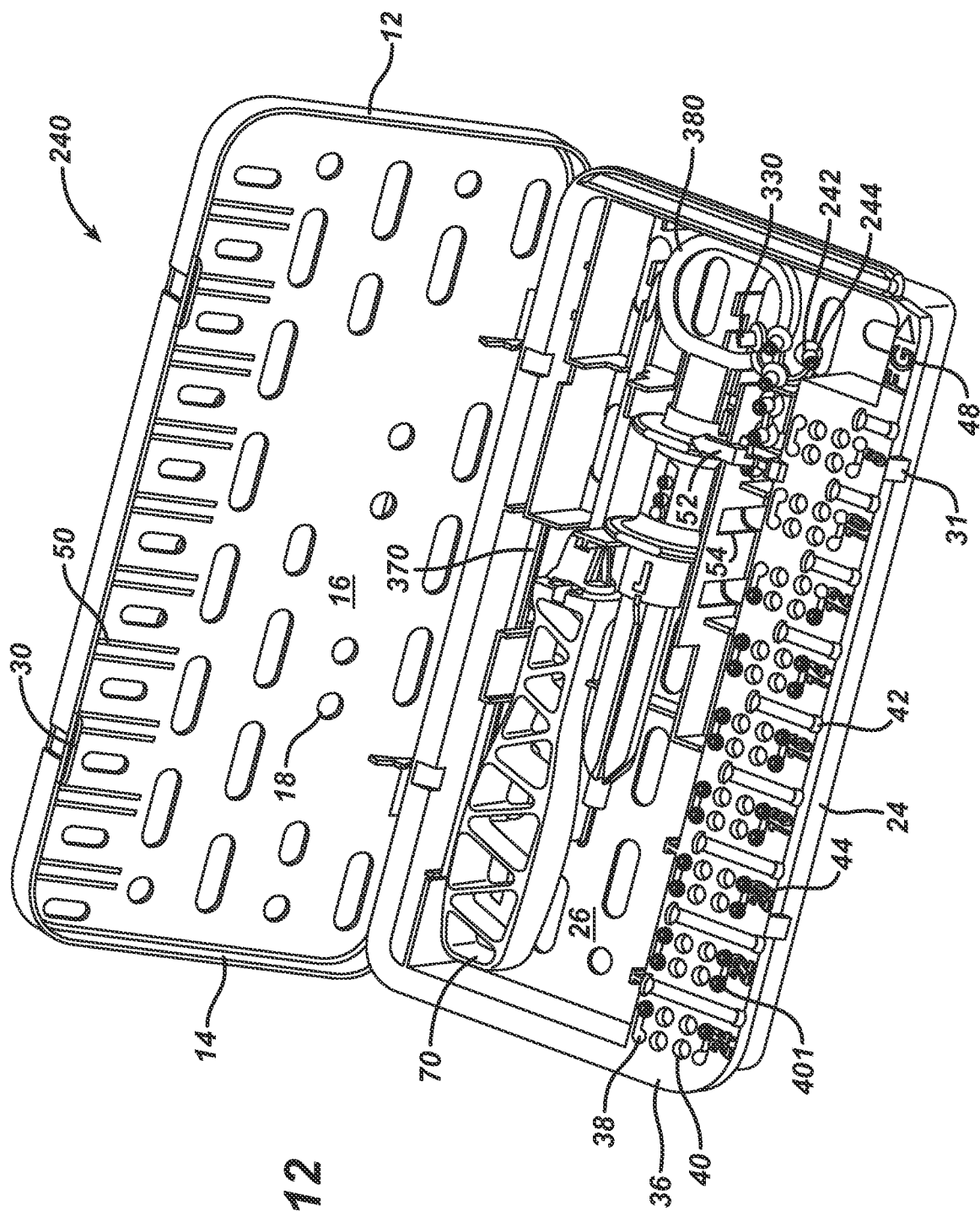
FIG. 12 is a top perspective view of a single-use, proximal radius kit.
Figure 13:
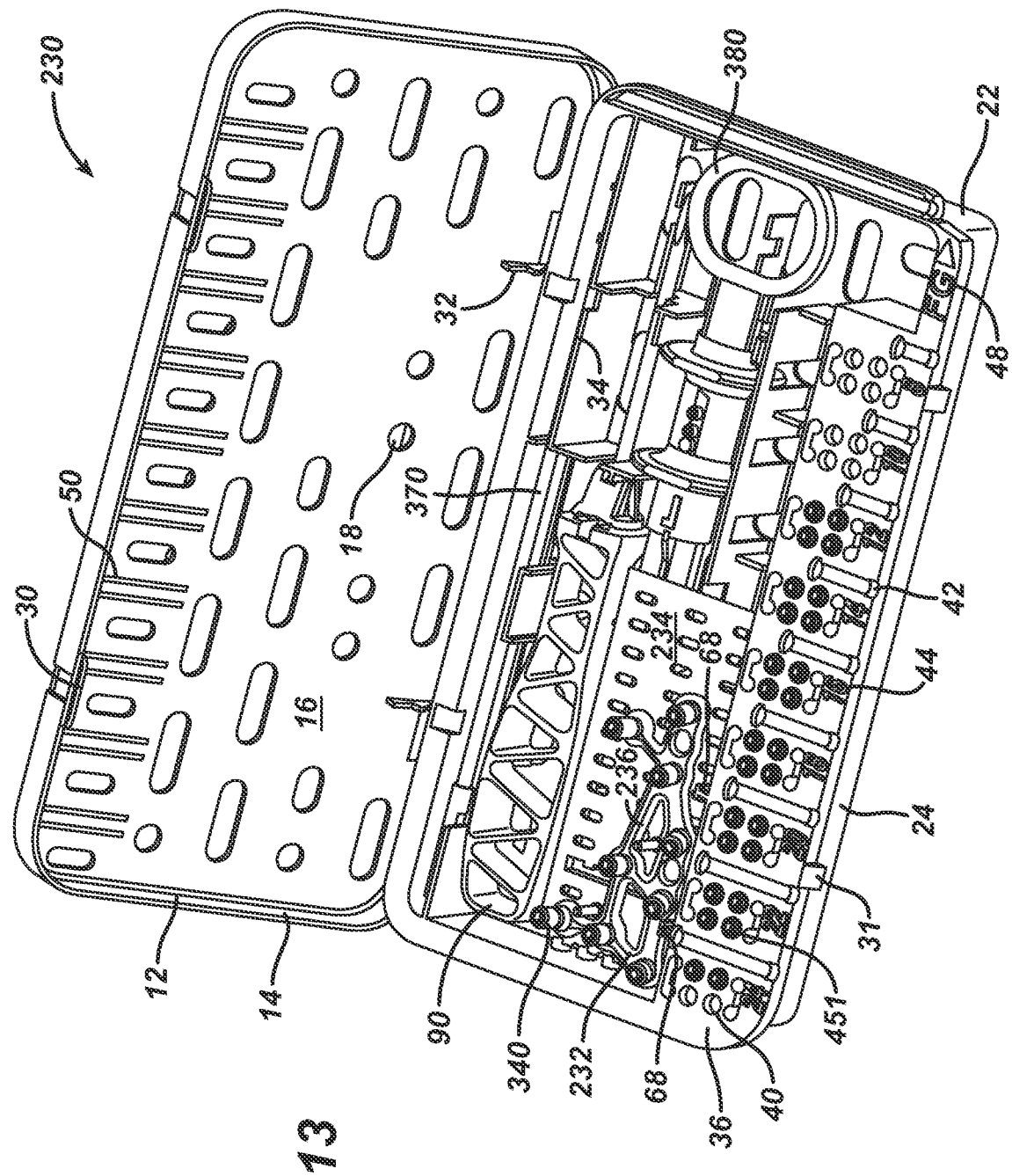
FIG. 13 is a top perspective view of a navicular kit.

Container 10, due to its versatility in design, may be used to contain many different combinations of components, depending on the surgical indication, for at least each of the single-use kit embodiments described herein. FIGS. 4, 8, 9, 10, 11, 12 and 13 show a few of the possible, single-use kit embodiments and may be referenced in combination. Each of these single-use kits is configured for a surgical procedure for the internal fixation of a particular bone of the arm, leg, hand or foot. FIG. 4 shows a distal volar radius kit 100 (or DVR kit 100) for a fracture of the distal radius of the forearm; FIG. 8 shows a single use, DVR Long kit, also for a fracture of the distal radius of the forearm; FIG. 9 shows a single-use, fibula kit for a fracture of the fibula of the lower leg; FIG. 10 shows a single-use, dorsal nail plate kit 210 (or DNP kit 210) for a fracture of the distal radius of the forearm; FIG. 11 shows a single-use, flexible fracture fixation kit 220 (or F3 kit 220) for a fracture of a small bone, such as of the hand or foot; FIG. 12 shows a single-use, proximal radius kit 240 for a fracture of the proximal radius bone at the elbow; FIG. 13 shows a single-use, navicular kit 230 for a fracture of the navicular bone of the foot.

Figure 5:
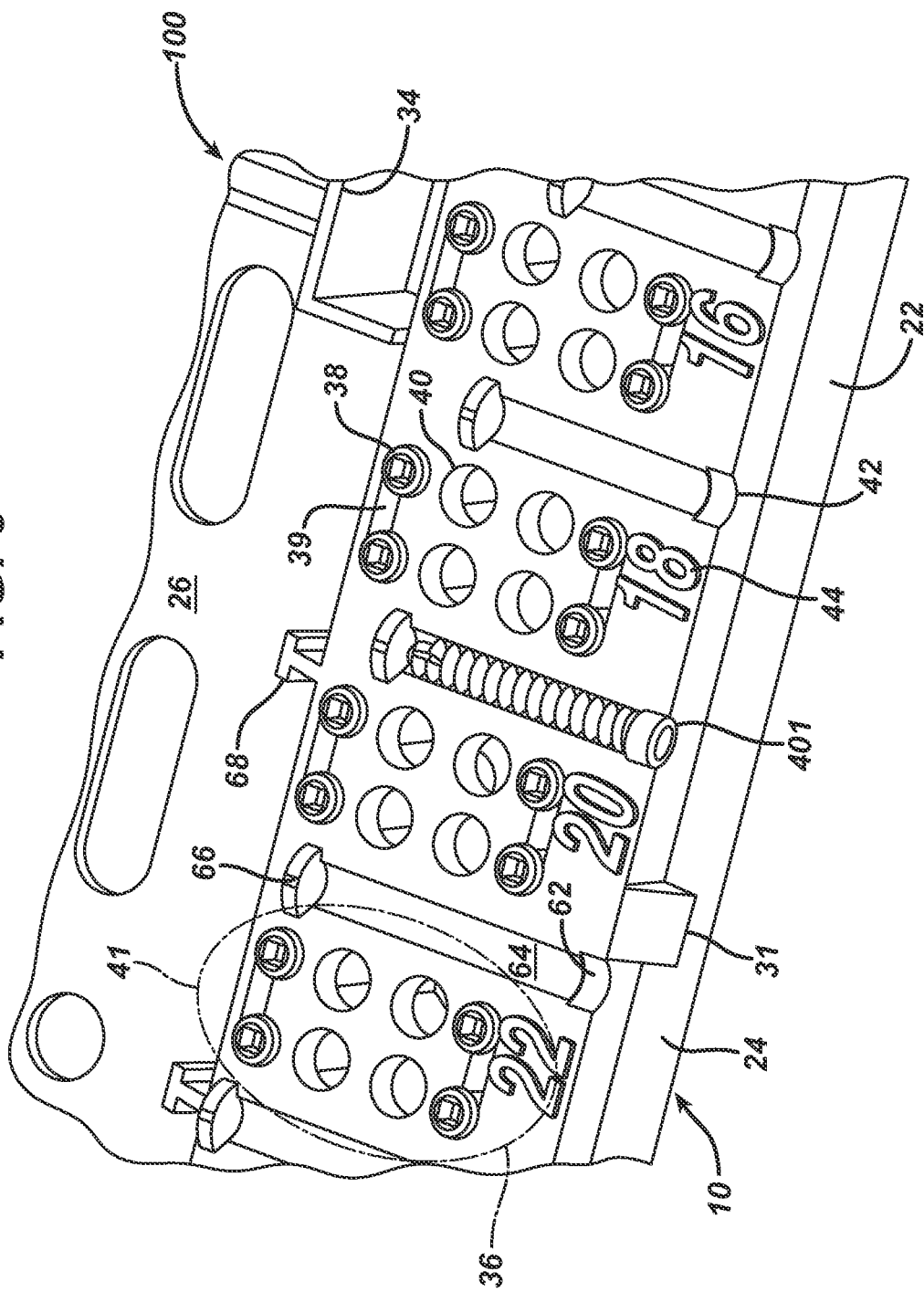
FIG. 5 is a top perspective, detailed view of part of the DVR kit of FIG. 4, showing a first fastener positioned in a fastener length gage.

As shown in FIG. 4 and also in the detailed view of FIG. 5, shelf 36 includes a plurality of first receptacles 38 and a plurality of second receptacles 40. Each of first receptacles 38 is sized and shaped to loosely retain first fastener 401, which has a nominal size, for example, of 2.7 mm, and each of second receptacles 40 is sized and shaped to loosely retain second fastener 451, which has a larger nominal size, for example, of 3.5 mm. First receptacles 38 is integrally formed in lid 12, wherein each pair of first receptacles 38 is connected by a bridge slot 39 to facilitate injection molding. Lid 12 includes a plurality of ribs 50 integrally formed into top portion 16, such that when lid 12 is in a closed position as shown in FIG. 2, each of ribs 50 abuts the exposed end of one of first fasteners 401 and second fasteners 451, such that all of the fasteners are securely retained in container 10.

First fastener receptacles 38 and second fastener receptacles 40 may be arranged such that plurality of first fasteners 401 and plurality of second fasteners 451 may be arranged in tray 22 in a plurality of groupings of eight or fewer fasteners. Each grouping corresponds to a particular one of a number of distinct fastener lengths. As shown in the present example, receptacles 38 and receptacles 40 are arranged in groupings, such that each grouping may contain up to eight fasteners (four of first fasteners 401 and four of second fastener 451) of the same shaft length. The number of receptacles within each groupings may vary in other embodiments. For example, each grouping may include two, four or six receptacles for containing fasteners.

When lid 12 is opened, the user may easily grasp the exposed end of each fastener and remove it from shelf 36. Alternately, the user may pick each fastener from shelf 36 using the drive instrument to be described. Since each single-use kit may include only the number of first fasteners 401 and second fasteners 451 required for the particular surgical indication, with a few extra, a number of first receptacles 38 and second receptacles 40 may be empty.

Also as shown in FIGS. 4 and 5, shelf 36 includes a plurality of fastener length gages 42, each of which is configured and labeled by a size label 44 for measuring incremental lengths of first fasteners 401 and second fasteners 451. The incremental lengths may range, for example, between 8 mm and 24 mm by 2 mm increments. Each of length gages 42 has a seat 62, a channel 64 and a stop 66. As shown in FIG. 5, when first fastener 401 of a particular, incremental length is mated into the appropriate one of gages 42, first fastener 401 fully fills that particular length gage without extending beyond seat 62. Using length gages 42, the surgeon may quickly confirm the length of a selected fastener prior to implantation of the fastener into the patient, thus ensuring that the fastener is of sufficient length to properly engage bone, but not so long as to protrude too far from the bone and into soft tissue.

Still referring to FIG. 4, DVR kit 100 includes container 10 and a plurality of components that include a first DVR assembly 102, a plurality of first fasteners 401, and a first drive instrument 70. The surgeon may use first driver instrument 70 to transmit a torque and drive each of first fasteners 401 into bone. The plurality of components of DVR kit 100 includes a depth gage 380 and at least one drill wire 370. Each of the single-use kit embodiments disclosed herein contains a vertically stacked, plurality of wire drills 370 that are retained between one of tray sides 24 and one of partitions 34 of tray 22, such that the tips of wire drills 370 are shielded from the other components and the user's hands.

As shown in FIG. 4, DVR kit 100 includes twenty-four of first fasteners 401, although the quantity may vary. An appropriate quantity of first fasteners 401 of various lengths may be based on historical data for similar, distal volar radius fracture procedures, with a few more fasteners provide to allow for special circumstances (dropped or damaged fasteners, unusual fractures, etc.).

First DVR assembly 102 includes a first DVR bone plate 104 preassembled with a plurality of first drill guides 330. The surgeon may use such preassembled drill guides to guide a wire drill when drilling holes into the fractured bone, so that the drilled holes are properly aligned with the apertures of the bone plate, and while also protecting the internal threads of the apertures. Such preassembled drill guides may also be useful for reshaping the bone plate using special bending instruments that fit over the drill guides. After drilling each hole, the surgeon may insert a drive end 80 of drive instrument 70 into drill guide 330 and remove drill guide 130 from plate 104.

Figure 6:
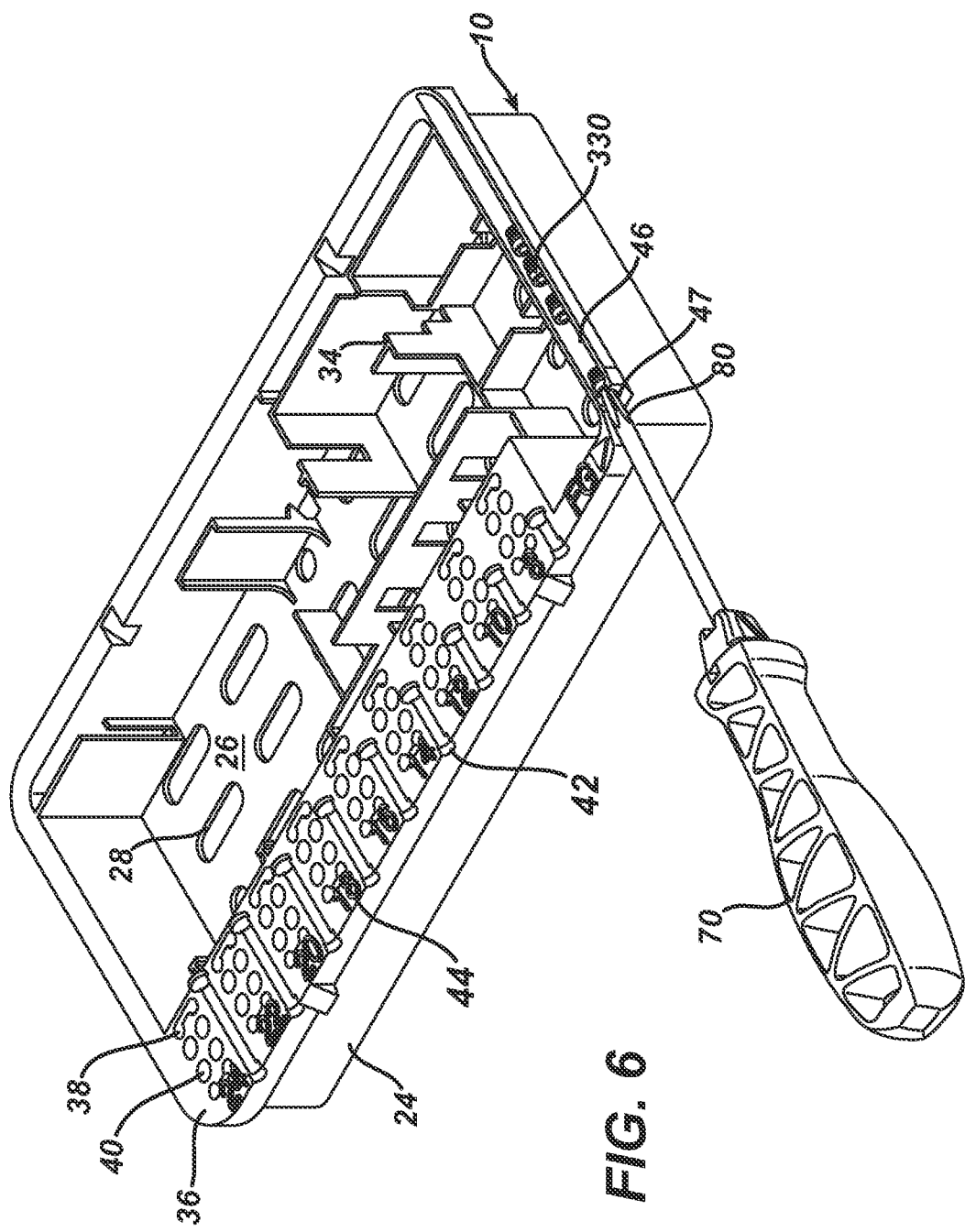
FIG. 6 is a top perspective, detailed view of another part of the DVR kit of FIG. 4, showing a drill guide as it is removed from a driver and placed into a reservoir of the container.

As shown in FIG. 6, each of a reservoir 46 and a stripping slot 47 is integrally formed into container 10. The surgeon may use stripping slot 47 to remove drill guide 330 from drive instrument 70, such that drill guide 330 falls into reservoir 46. In the embodiment shown, the user may collect a plurality of drill guides in a easily visible, linear arrangement, such that the user can quickly account for the number of drill guides 330 that have been removed from plate 104. An instructive label 48 (the letters "FG" stand for Fast Guide™) aids the "first-time" user in understanding where to discard drill guides 330.

Figure 7:
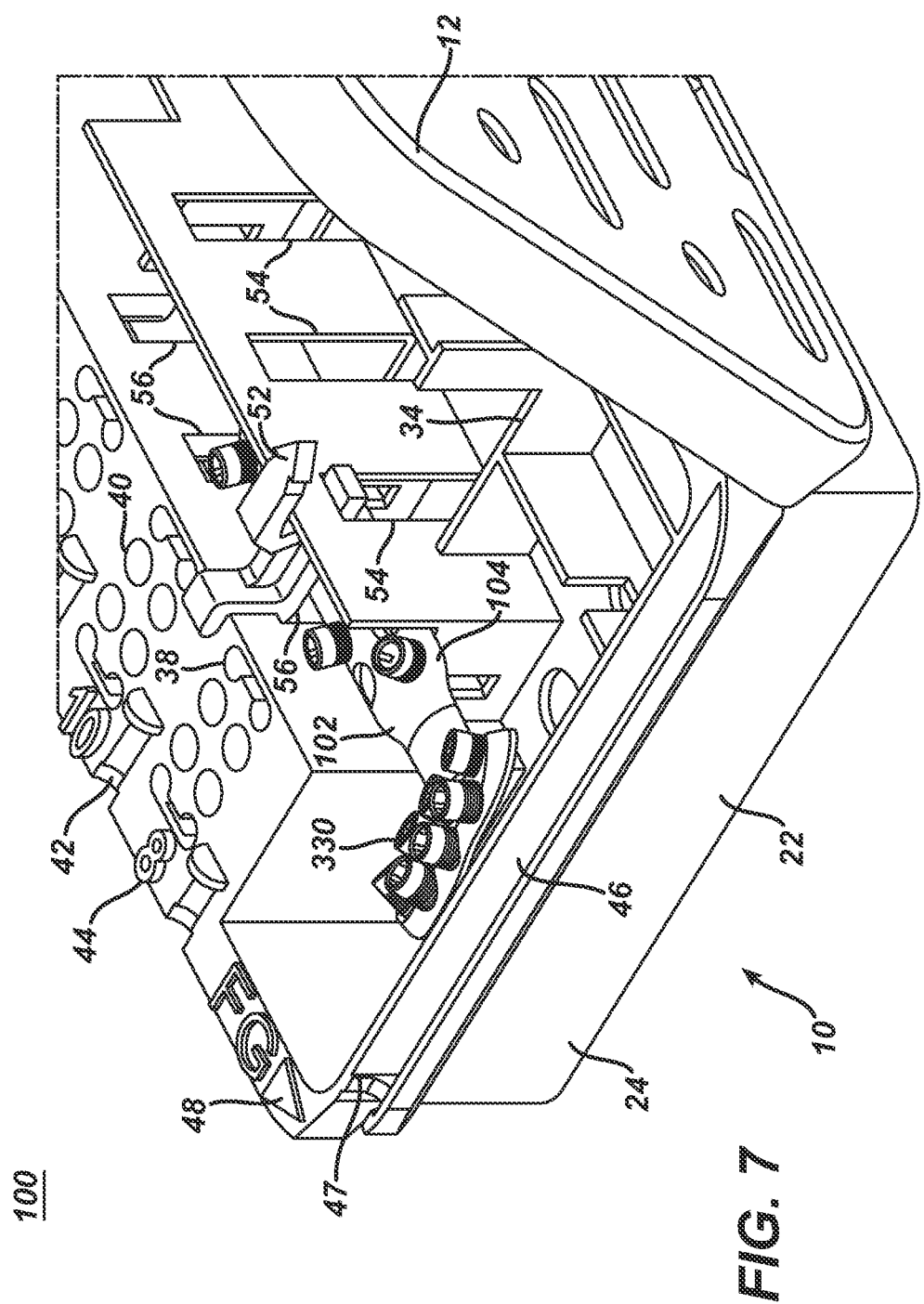
FIG. 7 is a top perspective, detailed view of another part of the DVR kit of FIG. 4, showing a retaining clip holding a DVR assembly in the container.

FIG. 7 is a top perspective, detailed view of part of DVR kit 100, showing a retaining clip 52 holding DVR assembly 100 between partitions 34 of container 10. First slots 54 and second slots 56 are formed into container 10, and clip 52 is configured, such that clip 52 may removably lock into one of first slots 54 and its opposing one of second slots 56. Clip 52 straddles over and retains DVR assembly 100, and is easily removable so that DVR assembly 100 may be lifted out of container 10. When container 10 is in the closed configuration, lid 12 abuts and holds clip 52 in place. In this embodiment of container 10, three pairs of slots 54 and 56 are provided to allow placement of clip 52 in three different positions. This allows container 10 to have the versatility to contain different types of bone plate assemblies.

FIG. 8 is a top perspective view of the single-use, DVR long 490 kit, which includes container 10 and a plurality of components, including a DVR long plate assembly 492, a plurality of first fasteners 401, a plurality of second fasteners 451, a plurality of wire drills 370, a second driver 90 and a depth gage 380. DVR long plate assembly 492 includes a plurality of first drill guides 330 preassembled to a DVR long plate 494. DVR long plate 494 includes a plurality of apertures of different types to be described, such that the user may attach DVR long plate 494 to the fractured bone using at least a portion of each of the plurality of first fasteners 401 and the plurality of second fasteners 451. (All bone plate apertures described herein should be understood to be fastener apertures, as opposed to K-wire apertures, suturing apertures, etc.)

FIG. 9 is a top perspective view of the single-use, fibula kit 200, which includes container 10 and a plurality of components, including a fibula plate assembly 202, plurality of first fasteners 401, plurality of second fasteners 451, plurality of wire drills 370, second driver 90 and depth gage 380. Fibula plate assembly 202 includes a plurality of second drill guides 340 preassembled to a fibula plate 204. Fibula plate 202 includes a plurality of apertures of different types to be described, such that the user may attach fibula plate 204 to the fractured bone using at least a portion of each of the plurality of first fasteners 401 and the plurality of second fasteners 451.

FIG. 10 is a top perspective view of the single-use, dorsal nail plate 210 (or DNP) kit, which includes container 10 and a plurality of components, including a DNP plate assembly 212, a plurality of first fasteners 401, a plurality of wire drills 370, first driver 70 and depth gage 380. Nail plate assembly 212 includes a DNP plate 494 removably attached to a DNP handle 216. DNP plate 494 includes a plurality of apertures to be described, such that the user may attach DNP plate 494 to the fractured bone using at least a portion of each of the plurality of first fasteners 401.

FIG. 11 is a top perspective view of the single-use, flexible fragment fixation (or F3) kit 220, which includes container 10 and a plurality of components, including a F3 plate assembly 222, plurality of first fasteners 401, plurality of wire drills 370, first driver 70 and depth gage 380. F3 plate assembly 222 includes a F3 plate 224 having a plurality of apertures to be described, such that the user may attach F3 plate 224 to the fractured bone using at least a portion of each of the plurality of first fasteners 401. F3 kit 220 is particularly suitable for the internal fixation of a fractured, distal ulna bone, and therefore may also be referred to as a distal ulna kit.

FIG. 12 is a top perspective view of the single-use, proximal radius kit 240, which includes container 10 and a plurality of components, including a proximal radius plate assembly 242, a plurality of first fasteners 401, a plurality of wire drills 370, first driver 70 and depth gage 380. Proximal radius plate assembly 242 includes a proximal radius plate 244 having a plurality of apertures to be described, such that the user may attach proximal radius plate 244 to the fractured bone using at least a portion of each of the plurality of first fasteners 401.

FIG. 13 is a top perspective view of the navicular kit 230, which includes container 10 and a plurality of components, including a navicular plate assembly 230, a plurality of second fasteners 451, a plurality of wire drills 370, second driver 90 and depth gage 380. Navicular plate assembly 230 includes a plurality of second drill guides 340 preassembled with a navicular plate 236 having a plurality of apertures to be described, such that the user may attach navicular plate 244 to the fractured bone using at least a portion of each of the plurality of first fasteners 401. Navicular plate assembly 232 is removably retained upon a board insert 234 that, in turn, is retained within container 10 by a pair of T-rails 68 integrally formed into container 10.

Figure 14:
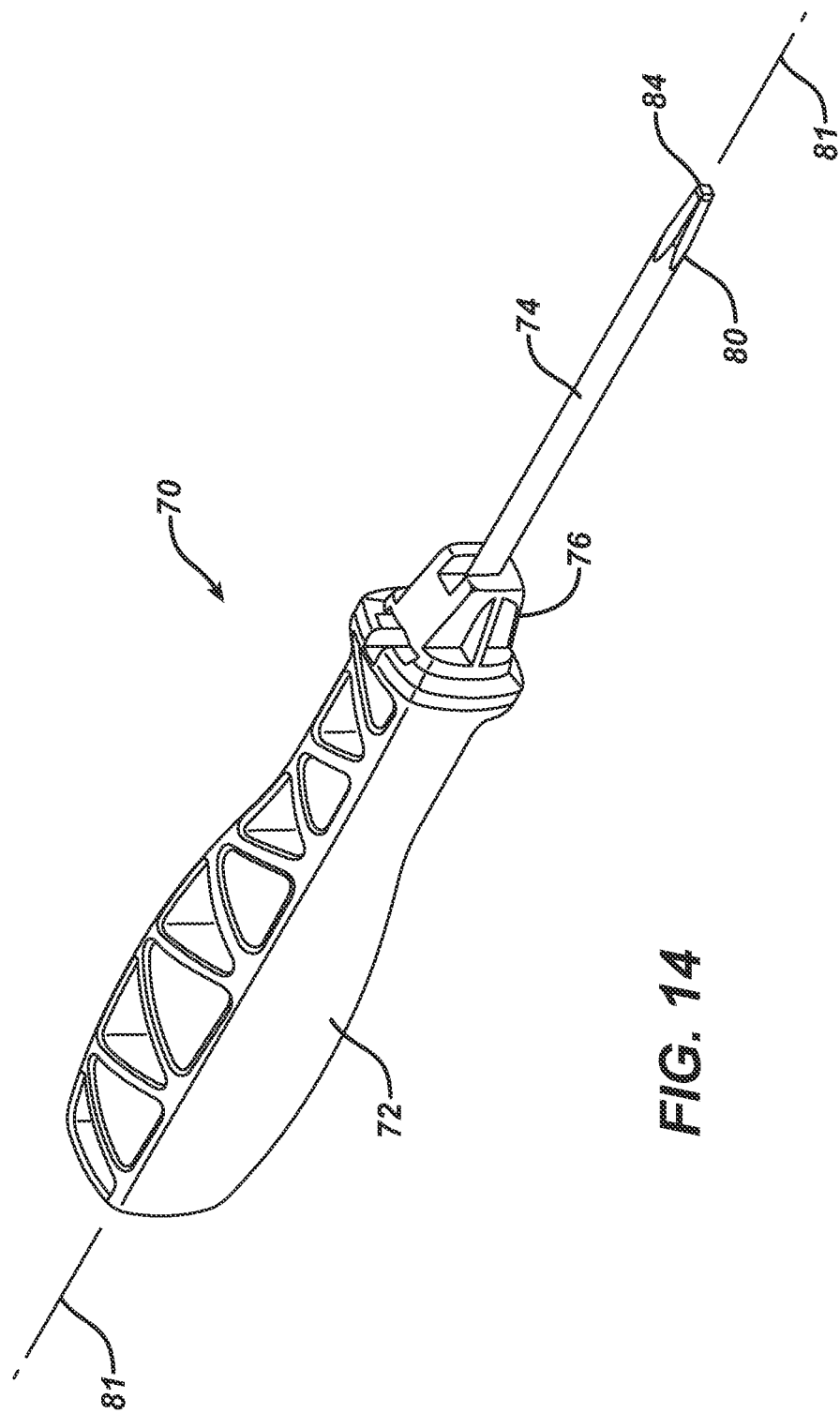
FIG. 14 is a perspective view of a first drive instrument, which has a first drive tip.

FIG. 14 is a perspective view of first drive instrument 70, which has a handle 72 connected by an attachment 76 to a shaft 74 that defines a longitudinal axis 81. At the distal end of shaft 74 is a first drive end 80 that includes a first drive tip 84. Handle 72 may be formed from a rigid, high strength polymer. Shaft 74 may be formed from a stainless steel and has a proximal end (not visible in the figures) that is configured to be retainably insert-molded into handle 72 at attachment 76. As will be further described in conjunction with FIG. 25, first drive tip 84 is configured for use with first fastener 401.

Figure 15:
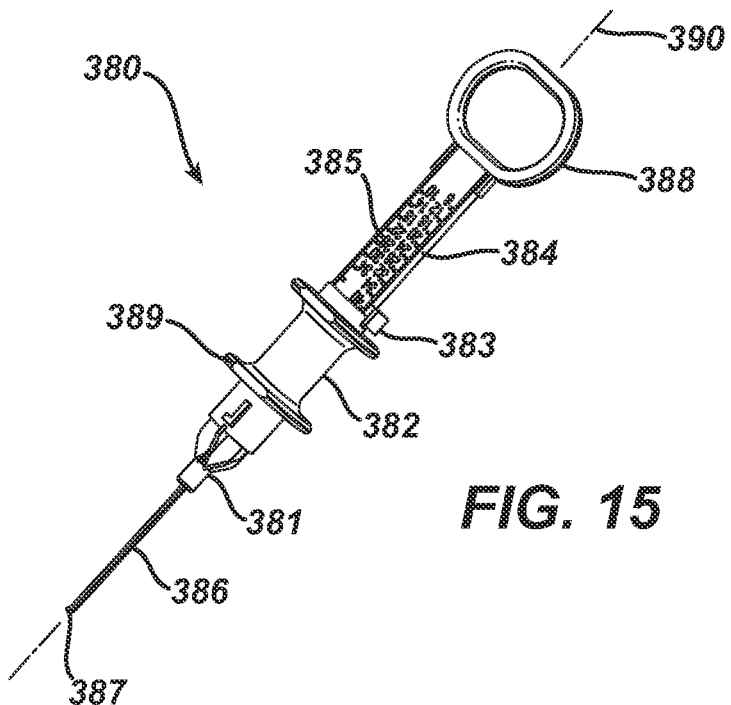
FIG. 15 is a perspective view of a depth gage for measuring the length of a hole extending through an aperture of a bone plate and a coaxially drilled hole in the bone, the depth gage shown in an extended position.
Figure 16:
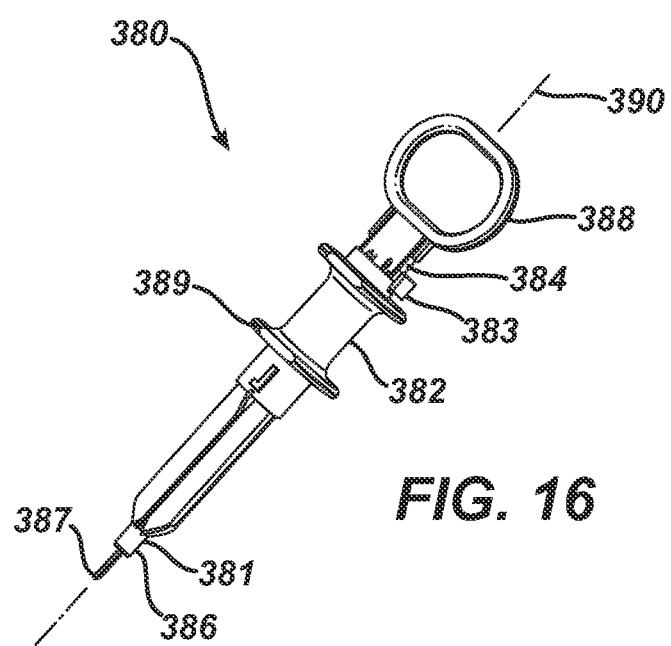
FIG. 16 is a perspective view of the depth gage of FIG. 15, shown in a retracted position.

FIG. 15 is a perspective view of depth gage 380 for measuring the length of a hole extending through an aperture of a bone plate and a coaxially drilled hole in the bone, shown in an extended position. FIG. 16 is a perspective view of depth gage 380, shown in a retracted position. Depth gage 380 includes a body component 382 that frictionally fits over a slide component 384 having a distal and proximal end defining a longitudinal axis 390 therebetween. Body component 382 is adjustably movable along slide component 384 along longitudinal axis 390. Each of body component 382 and slide component 384 may be injection molded from a rigid polymer. A feeler wire 386, which may be formed from stainless steel, is attached to body component 382 and extends distally along longitudinal axis 390 from the distal end of slide component 384. Feeler wire 386 includes a hook tip 387. A ring 388 is connected to the proximal end of slide component 384 and is sized and shaped for a thumb of the user. A spool portion 389 of body component 382 is sized and shaped for placement between, for example, the fore and middle fingers of the user. The slide component 384 includes indicia 385 that corresponds to the length of feeler wire 386 extending distally from the distal end of slide component 384. The position of body component 382 is adjustable between a first stop 381 and a second stop 383 on slide component 384. The frictional fit between slide component 384 and body component 382 is sufficient to maintain this position when the user releases depth gage 380.

The user may measure the length of the aperture through the plate and bone, and thereby determine the length of the fastener needed, by first fully extending feeler wire 386, then catching hook tip 387 on the edge of the aperture on the far side of the bone. Then the user adjusts spool portion 389 and ring 388 towards each other until the distal end of slide component 384 abuts the top surface of the bone plate. The user may read the indicia 385 that aligns with the proximal end of body component 382 and corresponds to the length of the aperture. Depth gage 42 may also be used through a drill guide preassembled to the plate, in which case, the user may read the indicia 385 that aligns with the proximal end of second stop 383.

Figure 17:
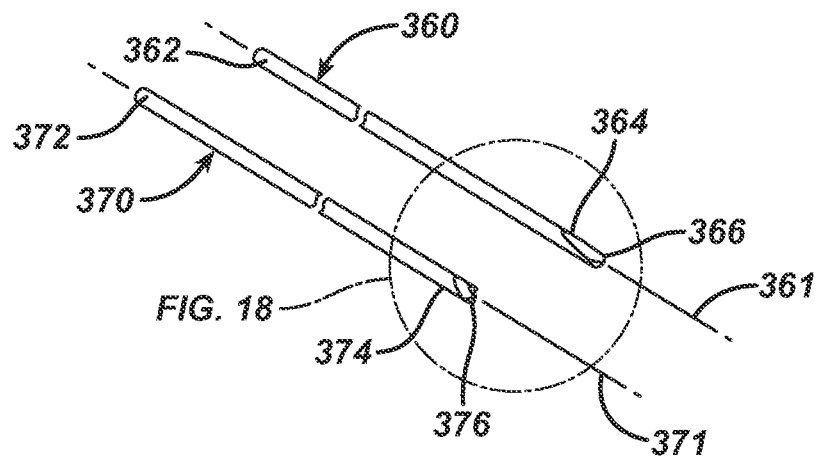
FIG. 17 is a perspective view of a pair of wire drills.
Figure 18:
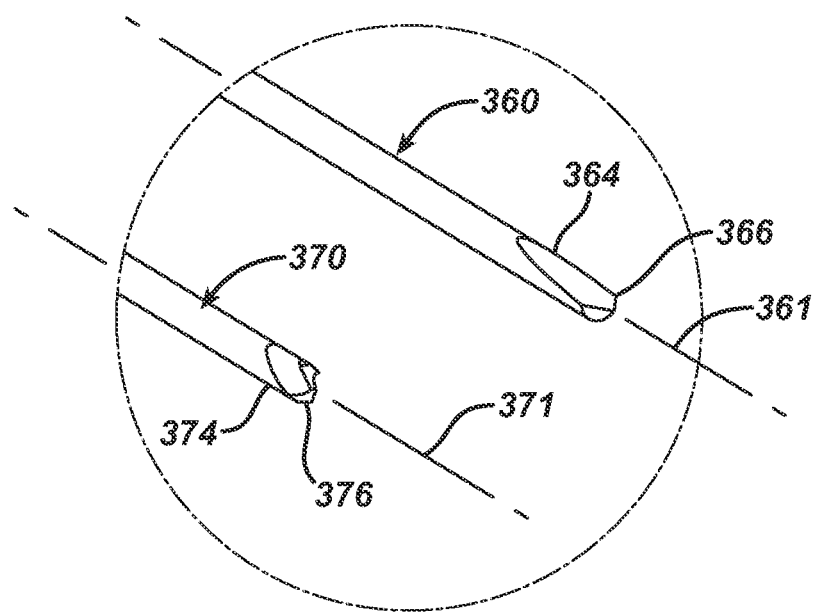
FIG. 18 is a perspective, detail view of the distal ends of the wire drills shown in FIG. 17.

FIG. 17 is a perspective view of wire drill 370 and an alternate wire drill 360. FIG. 18 is a perspective, detail view of the distal ends of wire drill 370 and alternate wire drill 360. Each of wire drill 370 and alternate wire drill 360 may be formed from a stainless steel and are well known in the art for drilling holes in bone, for the provisional fixation of fractured bones, for provisional attachment of bone plates to bone, and for other uses. Wire drill 370 has a proximal end 372, a distal end 373, a longitudinal axis 371 extending therebetween, and a fluted tip 376. Wire drill 360 has a proximal end 362, a distal end 364, a longitudinal axis 361 extending therebetween, and a spade tip 366. Each of the single-use kits disclosed herein may contain at least one of alternate wire drill 360 and/or at least one of wire drill 370. In general, wire drill 370 may be used to prepare a pilot hole in bone for one of first fastener 401 and second fastener 451, so the diameter of wire drill 370 is appropriately sized accordingly. One version of wire drill 360 may be what is known in the art as a K-wire, which is primarily used for provisional fixation, and may be provided, for example, with a diameter of about 1.6 mm. The surgeon may insert the K-wire through any one of the aforementioned apertures of the bone plates described herein, but it is well-known in the art that these plates may also include one or more smaller holes specifically for receiving K-wires and/or for attaching sutures thereto.

Figure 19:
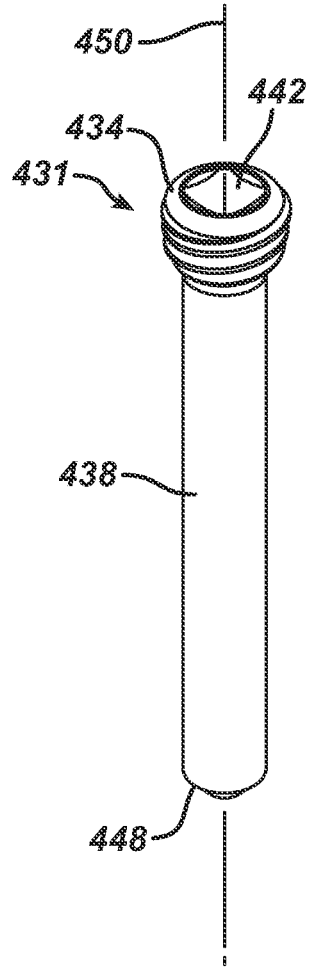
FIG. 19 is a perspective view of a first fastener, according to a second embodiment.
Figure 20:
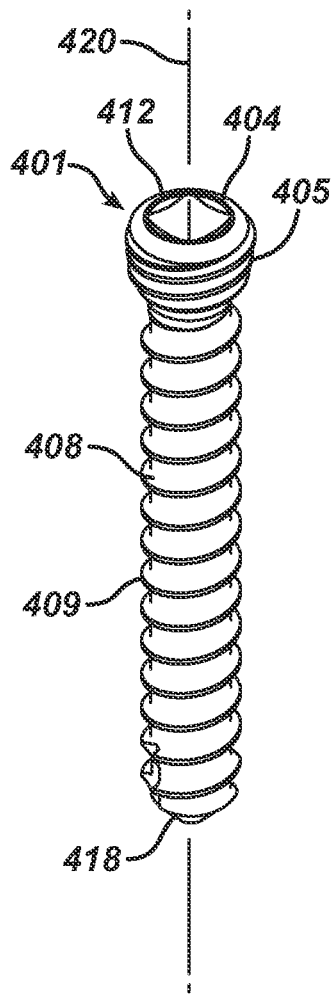
FIG. 20 is a perspective view of a first fastener, according to a first embodiment.
Figure 21:
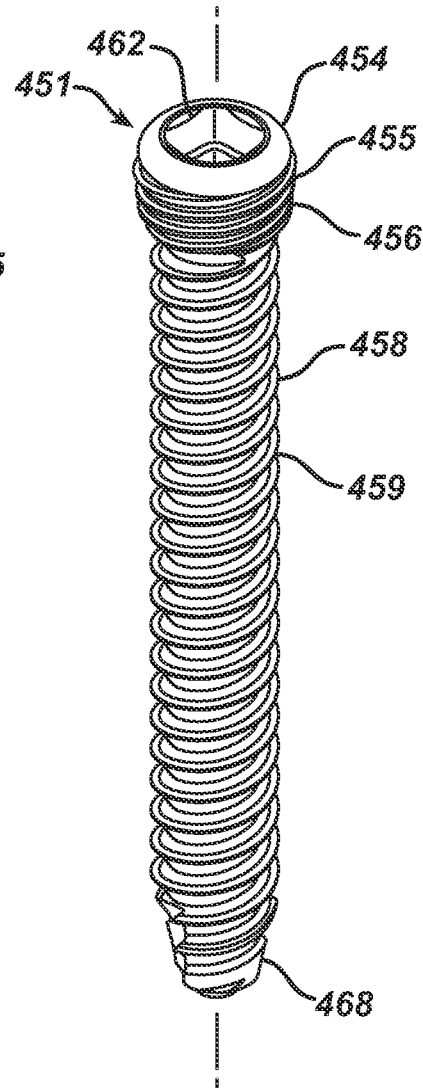
FIG. 21 is a perspective view of a second fastener.

FIGS. 19, 20 and 21 are perspective views of the same scale showing the fasteners that may be included in the single-use kits described herein. FIG. 20 is a perspective view of first fastener 401. FIG. 19 is a perspective view of an alternate embodiment of first fastener 401, also referred to as a first fastener peg 431. FIG. 21 is a perspective view of second fastener 451. Each of first fastener 401, first fastener peg 431 and second fastener 451 may be formed from a metal such as a titanium alloy such as Ti-6Al-4V that is anodized for anti-galling and abrasion resistance. First fastener 401 and first fastener peg 431 may have a nominal size of 2.7 mm and second fastener 451 may have a nominal size of 3.5 mm.

First fastener 401 has a head 404 and a shaft 408 that defines a longitudinal axis 420. Shaft 408 may be provided in a number of incremental lengths, ranging from 8 mm to 24 mm by increments of 2 mm, for example. Head 404 includes a plurality of external threads 405 and a drive socket 412 that has an approximately square configuration. Shaft 408 has a plurality of threads 409 and a tip 418 and is configured for self-tapping into a properly sized, drilled hole in the bone.

Figure 22:
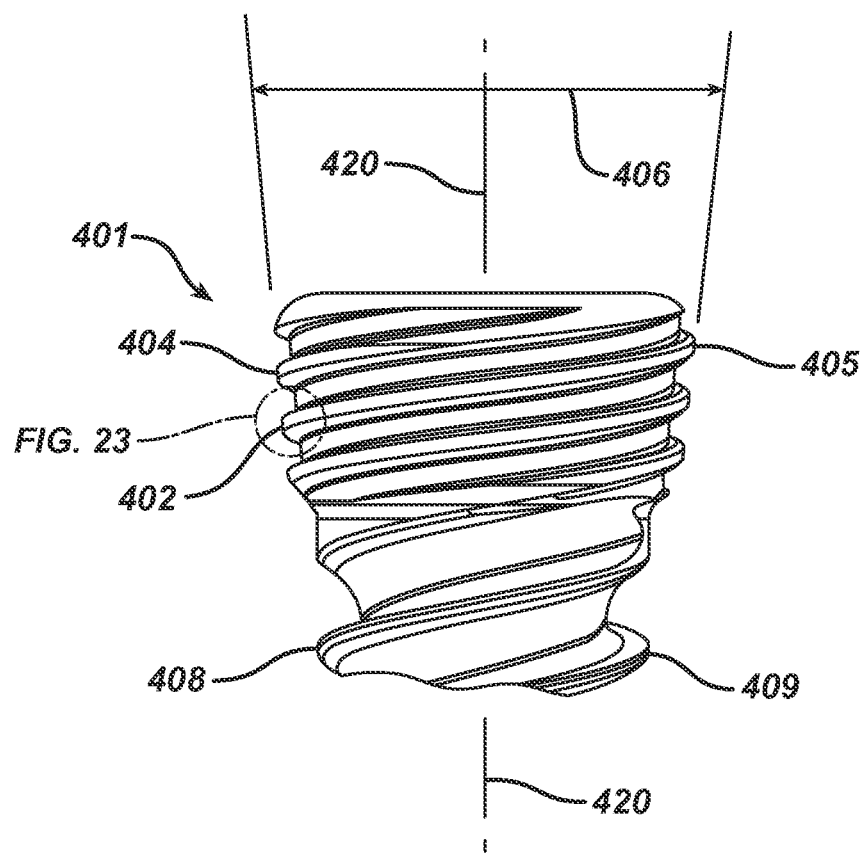
FIG. 22 is a detail view of a first tapered, threaded head of the first fastener shown in FIG. 20.
Figure 23:
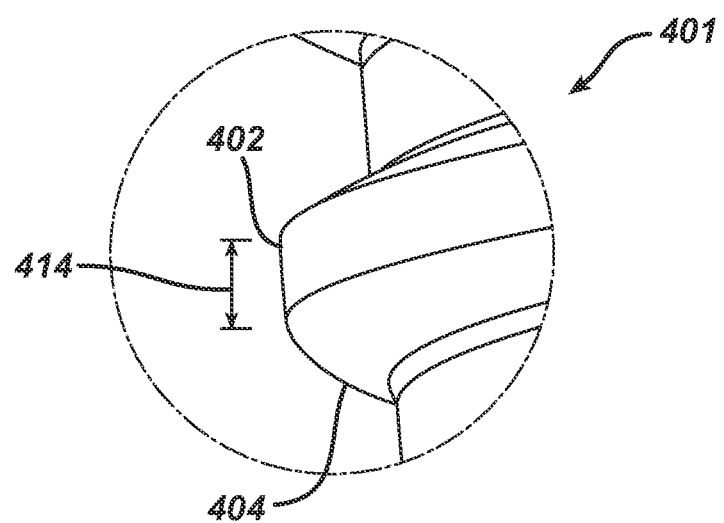
FIG. 23 is a detail view of a crest portion of a thread of the first tapered, threaded head of FIG. 22.

FIG. 22 is a detail view of head 404 of first fastener 401 shown in FIG. 20. Threads 405 are conically tapered and define a taper angle 406 of about 12 degrees, centered on longitudinal axis 420. Threads 405 may have a double-lead type of thread as shown in FIG. 22. Head 404 is adapted for locking at a fixed angle into a tapered, threaded (locking)

aperture of a bone plate, as is known in the art. But as will be described herein, head 404 is also adapted for use in particular non-threaded (non-locking) apertures. This is primarily due to the inclusion on threads 405 of crest portions 402 that have a crest width 414 (FIG. 23).

Crest width 414, as shown in FIG. 22, is 0.141 millimeters, but may be approximately in the range of 0.120 to 0.160 millimeters. A pitch distance between adjacent crest portions 402, as shown in FIG. 22, is 0.559, but may be approximately in the range of 0.500 to 0.600 millimeters. Therefore, a ratio of crest width 414 to pitch distance, as shown in FIG. 22, is 0.252, but may be approximately in the range of 0.200 to 0.320. Since crest portions 414 are relatively wide as compared to tapered, threaded heads of some currently available bone fasteners, first fastener 401 may be driven with high compressive force into a smooth (non-threaded) aperture in various trajectories, such that threads 405 are not "rolled over" or otherwise damaged during insertion. Without widened, crest portion 414 on threads 405, it may be more likely that head 404 would "pull through" the aperture of the plate under high compressive load.

First fastener peg 431, shown in FIG. 19, includes a head 434 having a drive socket 442 and may be identical to head 404 of first fastener 401. First fastener peg 431 also includes a smooth shaft 438, a rounded tip 448 and a longitudinal axis 450. Like shaft 408 of first fastener 401, shaft 438 may be provided in a number of incremental lengths, ranging from 8 mm to 24 mm by increments of 2 mm, for example. First fastener peg 431 is primarily used in locking (threaded) apertures.

As shown in FIG. 21, second fastener 451 includes a head 454, a shaft 458 and a longitudinal axis 470. Head 454 includes tapered threads 455 that may be a triple-lead type thread and include crest portions 456 that provide the same advantages as described for threads 405 of first fastener 401. As shown in FIG. 21, tapered threads 455 may have similar dimensions for crest width and pitch distance, as compared to first fastener 401 of FIG. 22. Shaft 458 has threads 459 and a tip 468 that may be conventionally designed for self-tapping into a drilled hole in the bone. Second fastener 451 may also be provided, for example, in the single-use kits described herein with lengths in the range of approximately 8 mm to 24 mm in 2 mm increments.

Figure 24:
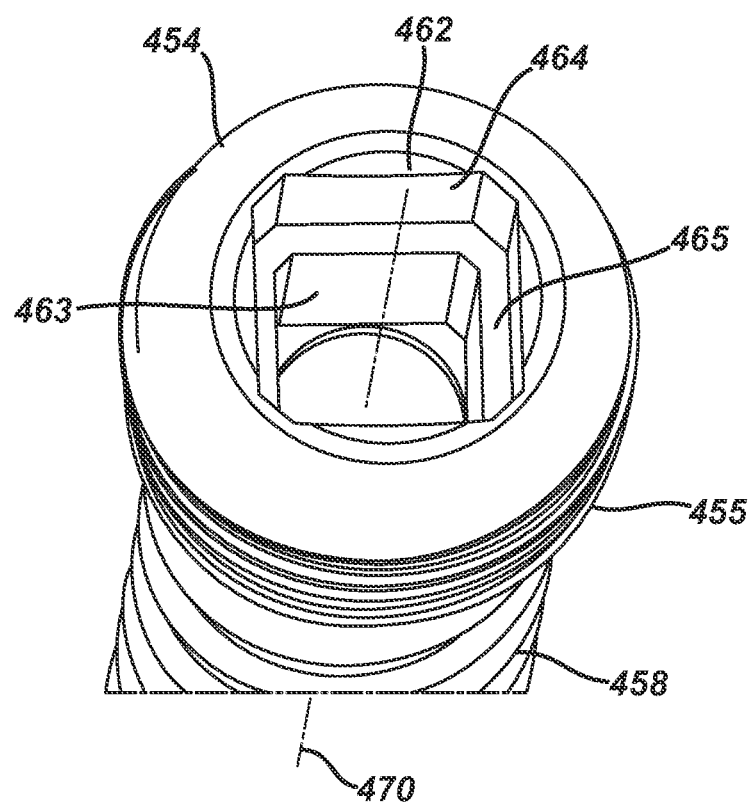
FIG. 24 is a perspective, detail view of a double socket of the second fastener shown in FIG. 21.

FIG. 24 is a perspective, detail view of head 454 and a portion of shaft 458 of second fastener 451 shown in FIG. 21. Head 454 includes a double-socket 462 that is sized and shaped for optimal use with second drive instrument 90 (to be described next for FIG. 26), although it may also be used with first drive instrument 70. Double-socket 462 includes a distal recess 463 that is adjacent and coaxial to a proximal recess 464 on longitudinal axis 470. Each of proximal recess 464 and distal recess 463 may have an approximately square configuration with each pair of opposing sides on proximal recess 464 parallel to a corresponding pair of opposing sides on distal recess 463. The height of distal recess 463 may be greater than the height of proximal recess 464. Proximal recess 464 is wider than distal recess 463, thereby forming a ledge 465 and fitting easily within the tapered shape of head 454 without weakening threads 455.

FIG. 25 is a perspective view of first drive end 80 of first drive instrument 70. FIG. 26 is a perspective view of second drive end 92 of second drive instrument 90. Each of first drive instrument 70 and second drive instrument 90, also referred to as torque drivers, may be use to drive each of first fastener 401 (including first fastener peg 431) and the larger, second fastener 451. However, second drive instrument 90 may be used to transmit more torque to second fastener 451 than what is possible using first drive instrument 70.

As shown in FIG. 25, drive end 80 includes a conical portion 88 that transitions distally, in the direction of axis 81, shaft 74 to a square taper portion 86, which in turn transitions to a square drive tip 84. When drive tip 84 is fully inserted into either one of drive socket 412 of first fastener 401 or double-socket 462 of second fastener 451, a portion of square taper 86 wedges into the non-tapered sidewalls of either drive socket 412 or double-socket 462, respectively. This feature causes either one of first fastener 401 or second fastener 451 to "stick" to the drive end of either one of first drive instrument 70 or second drive instrument 451, to facilitate removal of each fastener from container 10 and to position the fastener into one of the apertures of the bone plate and partially into the drilled hole in the bone prior to transmitting torque to drive the fastener into the bone.

As shown in FIG. 26, drive end 92 includes a first tapered square portion 95 that transitions distally, in the direction of axis 91, shaft 94 to a first square drive portion 96. A second tapered portion 97 extends distally along axis 91 to a second square drive portion 98 that is smaller than first square drive portion 96. When drive tip 92 is fully inserted into either one of drive socket 412 of first fastener 401 or double-socket 462 of second fastener 451, a portion of second square taper portion 97 wedges into the non-tapered sidewalls of either of drive socket 412 or double-socket 462, respectively. When drive end 92 is fully inserted into double-socket 462 of second fastener 451, at least one of first tapered portion 95 or second tapered portion 97 stick into double-socket 462. This also serves to aid the surgeon in the pick-up and placement of the fasteners. For obvious reasons, when a limited number of fasteners are readily available, it is highly desirable to avoid dropping fasteners into the wound site of the patient or onto a non-sterile surface in the operating room.

Figure 27:
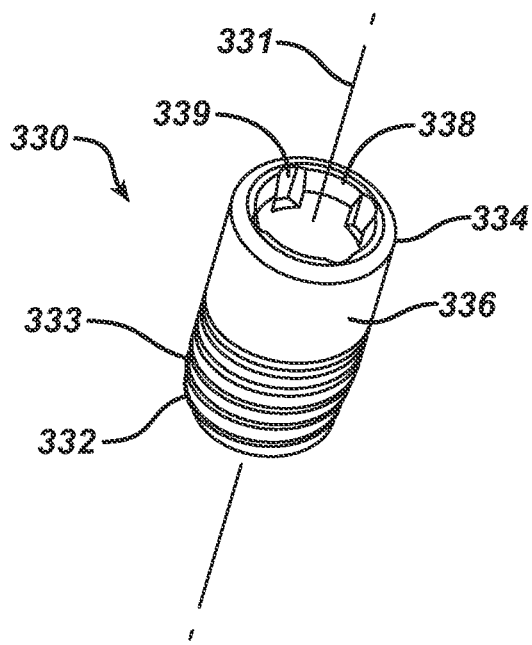
FIG. 27 is a perspective view of a first drill guide.

FIG. 27 is a perspective view of a first drill guide 330 for use with one of the appropriately sized, wire drills 370, to drill a hole into bone for receiving first fastener 401. A plurality of first drill guides 330 may be preassembled with bone plates as previously shown in FIGS. 4, 8, 11 and 12. First drill guide 330 includes a body 336 having a distal end 332, a proximal end 334, and a bore 338 sized and shaped to guide the appropriately sized wire drill 370 and defining a longitudinal axis 331. Distal end 332 includes threads 333 for removable attachment to a threaded aperture of a bone plate. Proximal end 334 includes four indentations 339 spaced evenly apart on the periphery of bore 338 for receiving square drive tip 84 of first drive instrument 70 and second drive portion 98 of second drive instrument 90.

Figure 28:
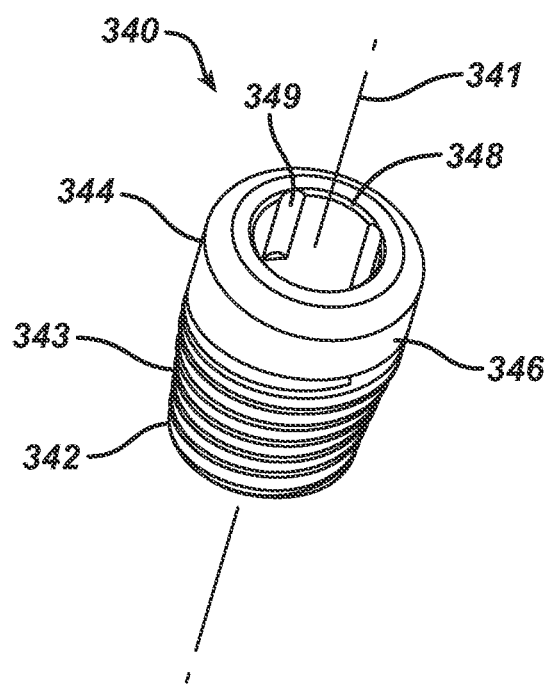
FIG. 28 is a perspective view of a second drill guide.

FIG. 28 is a perspective view of a second drill guide 340 for use with one of the appropriately sized, wire drills 370, to drill a hole into bone for receiving second fastener 451. A plurality of second drill guides 340 may be preassembled with bone plates as previously shown in FIGS. 9 and 13. Second drill guide 340 includes a body 346 having a distal end 342, a proximal end 344, and a bore 348 sized and shaped to guide the appropriately sized wire drill 370 and defining a longitudinal axis 341. Distal end 342 includes threads 343 for removable attachment to a threaded aperture of a bone plate. Proximal end 344 includes four indentations 349 spaced evenly apart on the periphery of bore 348 for receiving square drive tip 84 of first drive instrument 70 and second drive portion 98 of second drive instrument 90.

Figure 29:
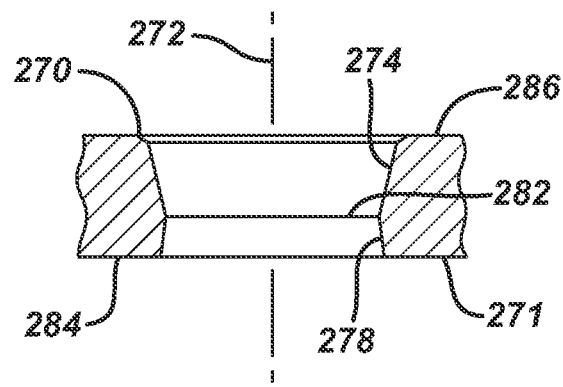
FIG. 29 is a cross-sectional view of a non-locking aperture.
Figure 30:
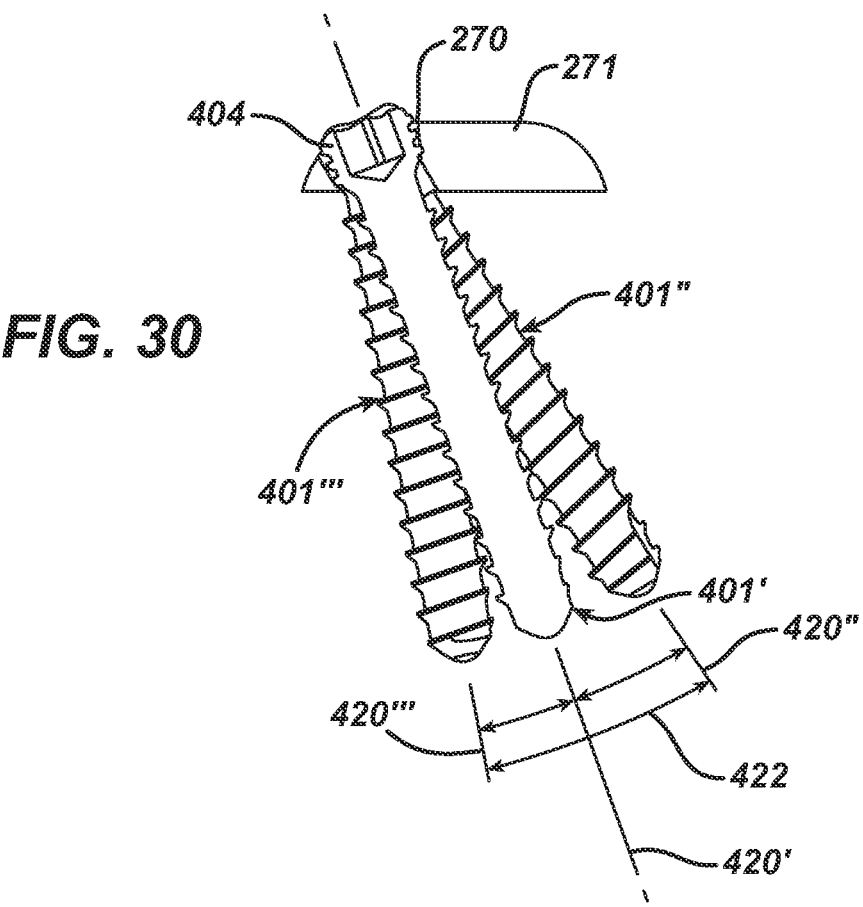
FIG. 30 is a cross-sectional view of a bone plate showing three possible trajectories of the first fastener of FIG. 20 inserted into the non-locking aperture of FIG. 29.

FIG. 29 is a cross-sectional view of a non-locking aperture 270 that may be sized to receive first fastener 401. (The term "aperture", as used herein, is interchangeable with the term "hole".) Similarly, although not shown in detail views in the figures, non-locking aperture 270 may also be sized to receive second fastener 451. FIG. 30 is a cross-sectional view of a portion of a bone plate 271 (for no particular surgical indication, but shown for description purposes), showing three possible trajectories of first fastener 401 of FIG. 20 inserted into non-locking aperture 270 of FIG. 29. Non-locking aperture 270 extends between a top surface 286 and a bottom surface 284 of a plate 271 and defines an axis 272. Non-locking aperture 270 has a conical upper portion 274 and tapers from top surface 286 towards the middle of plate 271. A conical lower portion 278 is coaxial with conical upper portion 274 and tapers from bottom surface 284 towards the middle of plate 271 to form a waist 282 with conical upper portion 274. The position and orientation of waist 282 relative to top surface 286 may vary, but as shown in FIG. 29, is deep enough to receive head 404 of first fastener 401, such that head 404 is not proud to top surface 286. As shown in FIG. 30, first fastener 401 may be inserted through plate 271 in any desired trajectory within a range defined by a conical angle 422, wherein axes 401', 401" and 401'" define three possible trajectories of first fastener 401 within that range. This multidirectional ability allows the surgeon to form a polyaxial non-locking compressive construct.

Figure 31:
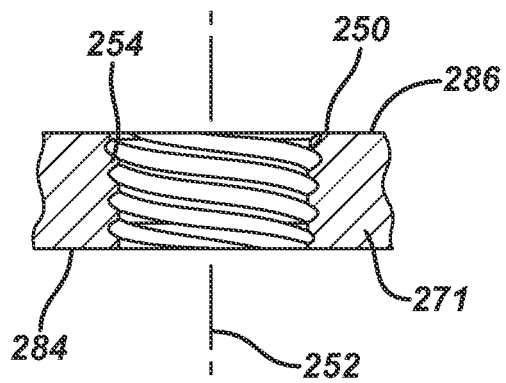
FIG. 31 is a cross-sectional view of a locking aperture.
Figure 32:
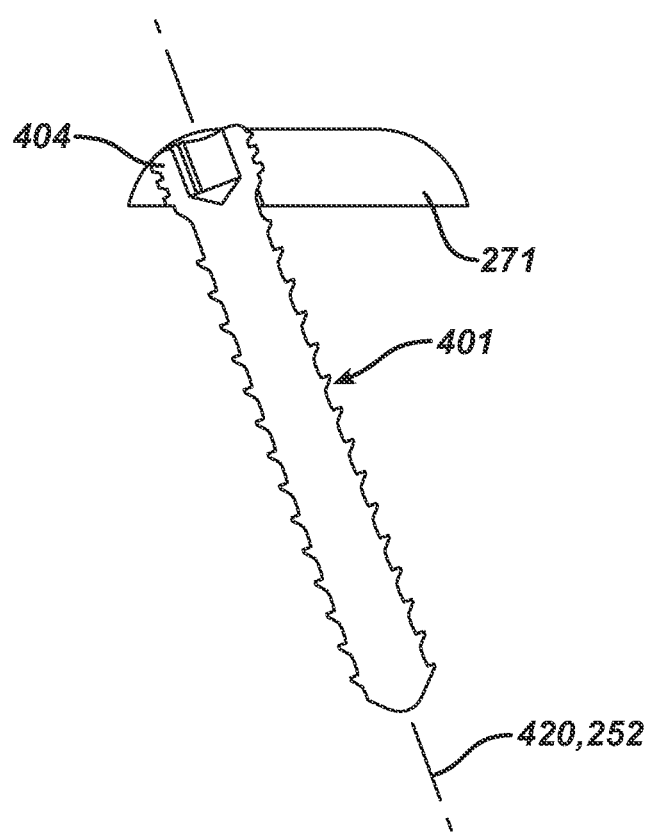
FIG. 32 is a cross-sectional view of a bone plate with the first fastener of FIG. 20 inserted at a fixed angle into the locking aperture of FIG. 31.

FIG. 31 is a cross-sectional view of a locking aperture 250, which is very similar to other locking apertures of bone plates that are well-known in the art. FIG. 32 is a cross-sectional view of bone plate 271 with first fastener 401 of FIG. 20 inserted at a fixed angle into locking aperture 250. Similarly, although not shown in detailed views in the figures, locking aperture 250 may be sized to receive second fastener 451. Locking aperture 250 includes a tapered, threaded bore 254 for receiving head 404 of first fastener 401. Bore 254 extends between top surface 286 and bottom surface 284 of plate 271 and defines an axis 252. As shown in FIG. 32, when first fastener 401 is fully inserted into plate 271, axis 420 of first fastener 401 is coaxial with axis 252 of locking aperture 250. This arrangement allows the surgeon to form a fixed-angle locking construct.

FIG. 33 is a top view of a unidirectionally ramped (or UR) aperture 290. FIG. 34 is a cross-sectional view of UR aperture 290. FIG. 35 is a cross-sectional view of UR aperture 290 with first fastener 401 partially inserted therein. FIG. 36 is a cross-sectional view of UR aperture 290 with first fastener 401 fully inserted therein. UR aperture 290 may also be sized, although not shown in detail views in the figures, to receive second fastener 451. UR aperture 290 is a non-locking type of aperture for compressively attaching the bone plate against the bone. The surgeon may also use UR aperture 290 to aid in reduction of the bone fragments, i.e., the compression of bone fragments along the longitudinal axis of the bone plate, often referred to in the art as dynamic compression. As shown in FIGS. 35 and 36, proper insertion of first fastener 401 into UR aperture 290 causes plate 271 to shift in a direction depending on the orientation of UR aperture 290. As shown in FIGS. 33 and 34, UR aperture 290 has an upper conical portion 294 intersecting with a coaxially opposing, lower conical portion 298 to form a waist 282 about an axis 292, in an arrangement similar to non-locking aperture 270 of FIG. 29. UR aperture 290 further includes a circular bore portion 306 defining an axis 307 that is parallel and offset from axis 308. Circular bore portion 306 is sized to receive shaft 408 of first fastener 401, but is too small to receive head 404. The surgeon may drill a hole into bone that is approximately coaxial with axis 307 and then insert first fastener 401 as shown in FIGS. 35 and 36, such that head 404 tends to seat into upper conical portion 294, and "ramp" in a translation direction along plate axis 272. The translation distance possible is determined by an offset distance 308 between axis 292 and 307.

Figure 37:
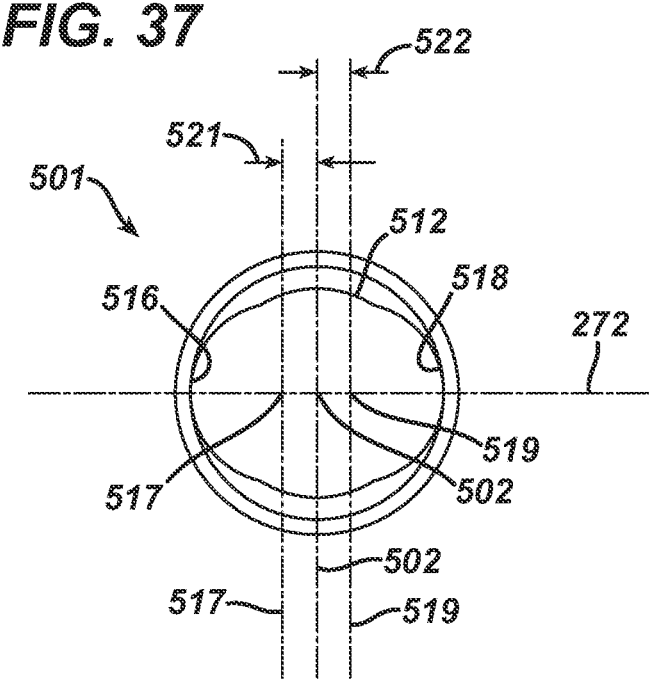
FIG. 37 is a top view of a bidirectionally ramped non-locking aperture.
Figure 38:
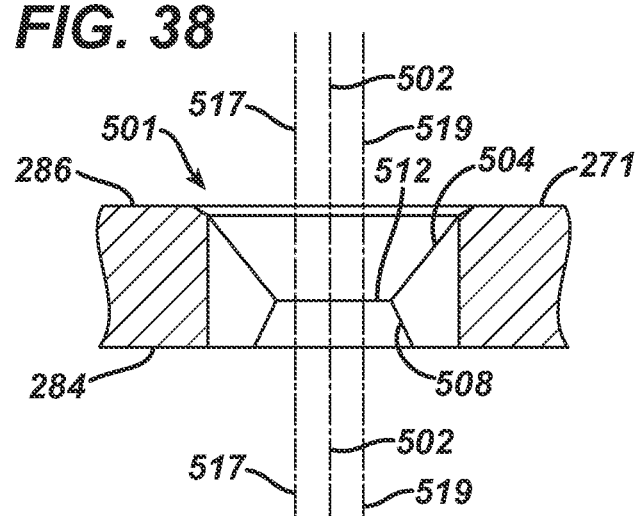
FIG. 38 is a cross-sectional view of the bidirectionally ramped non-locking aperture of FIG. 37.

FIG. 37 is a top view and FIG. 38 is a cross-sectional view of a bidirectionally ramped (BR) aperture 501, which is similar to UR aperture 290 of FIG. 34. BR aperture 501 may be sized to receive first fastener 401 or second fastener 451. The surgeon may use BR aperture 501 to compressively attach bone plate 271 against the bone, and also to dynamically compress the bone fragments along the longitudinal axis of plate 271 in either of opposing directions. This bidirectional feature allows the surgeon to reduce fragments on either side of BR aperture 501. BR aperture 501 includes an upper conical portion 504 defining an axis 502, a coaxial, lower conical portion 508, a waist 512, a first circular bore portion 516 defining an axis 517, and an opposing second circular bore portion 518 defining an axis 519. The surgeon may use BR aperture 501 with first fastener 401 to translate plate 271 an offset distance 521 in a first direction along axis 272 of plate 271, or an offset distance 522 in a second, opposing direction along axis 272.

FIG. 39 is a top view of a unidirectionally ramped (UR) slot 310 positioned along axis 272 of plate 271. FIG. 40 is a cross-sectional view of UR slot 310, taken through axis 272; FIG. 41 is a cross-sectional view of UR slot 310, taken through line 41-41 of FIG. 39; FIG. 42 is a top view of first fastener 401 partially inserted into UR slot 310; FIG. 43 is a top view of first fastener 401 fully inserted into the UR slot 310; FIG. 44 is a cross-sectional view, taken through axis 272, of first fastener 401 partially inserted into UR slot 310; FIG. 45 is a cross-sectional view, taken through axis 272, of first fastener 401 fully inserted into the UR slot 310. UR slot 310 is more elongated than UR aperture 290, and also may be used to dynamically compress bone fragments as first fastener 401 is inserted into bone. The use of slotted apertures similar to UR slot 310 in bone plates is well-known in the art for reducing bone fragments as the surgeon attaches the plate to the bone. UR slot 310 has an elongated, tapered portion 314 that defines a slot axis 315 and tapers from top surface 286 to bottom surface 284 of plate 271. A circular bore portion 312 is formed into one end of tapered portion 314 and is sized to receive shaft 408 of first fastener 401, but not head 404. As the surgeon inserts first fastener 401 into bone as shown in FIGS. 44 and 45, head 404 tends to seat into tapered portion 310 and move plate 271 in a direction along axis 272 a distance 317 (FIG. 45).

Figure 46:
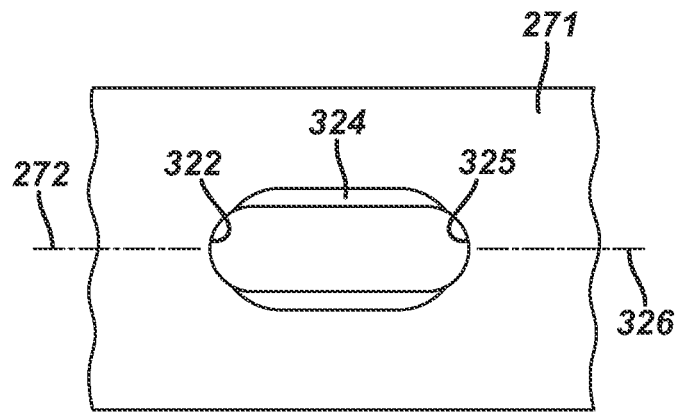
FIG. 46 is a top view of a bidirectionally ramped slot in a bone plate.
Figure 47:
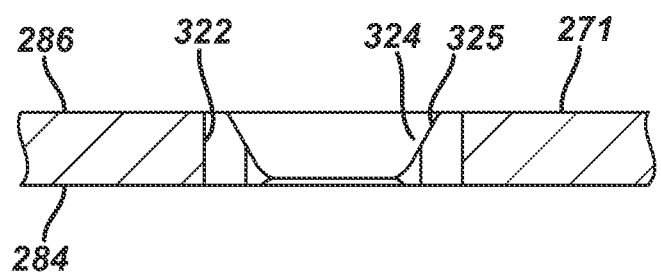
FIG. 47 is a cross-sectional view, taken through the longitudinal axis, of the bidirectionally ramped slot of FIG. 46.

FIGS. 46 and 47 shown a bidirectionally ramped (BR) slot 320 that is similar to UR slot 310, except the surgeon may use BR slot 320 to dynamically compress bone fragments in either of opposing directions along axis 292 of plate 271. BR slot 320 includes an elongated, tapered portion 325 that tapers from top surface 286 to bottom surface 284 of plate 271. A first circular bore portion 322 and a second circular bore portion 325 are formed into opposing ends of tapered portion 325.

Each of UR slot 310 and BR slot 320 may be sized to receive either first fastener 401 or second fastener 451.

Figure 49:
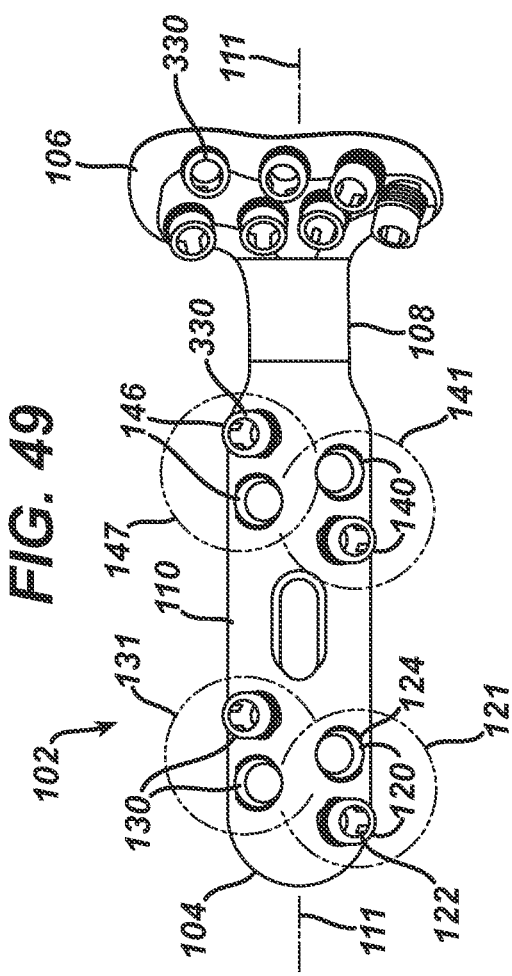
FIG. 49 is a top view of the first DVR assembly of FIG. 48.
Figure 48:
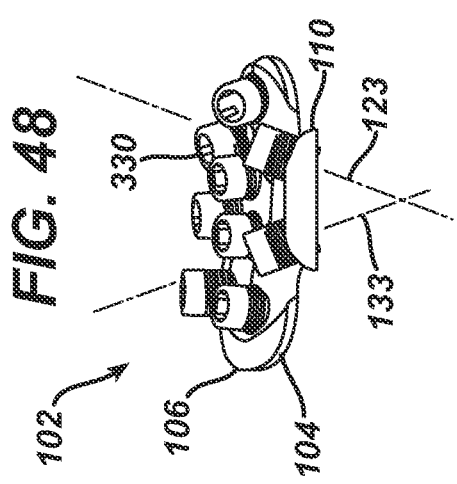
FIG. 48 is an end view of a first DVR assembly.
Figure 50:
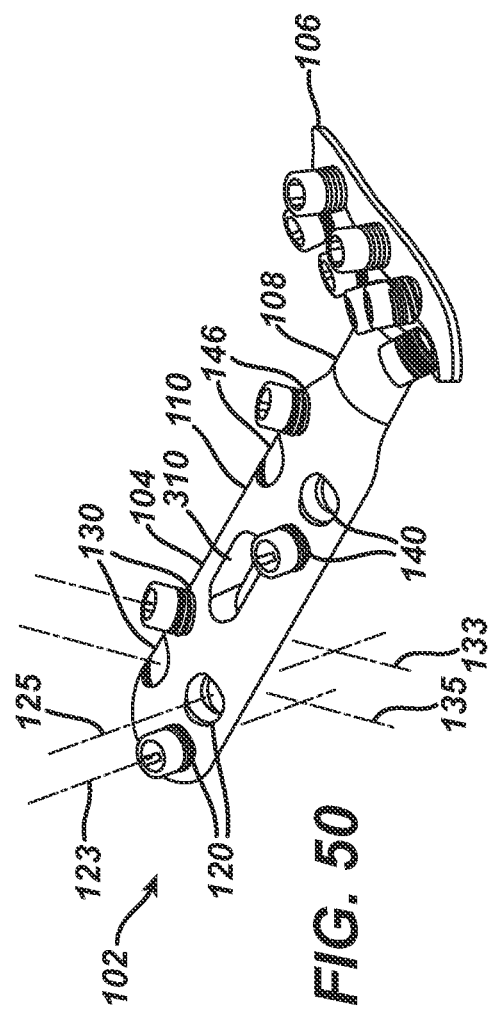
FIG. 50 is a perspective view of the first DVR assembly of FIG. 48.

FIG. 48 is an end view, FIG. 49 is a top view, and FIG. 50 is a perspective view of a first DVR assembly 102 that was earlier described for FIG. 4. First DVR assembly 102 includes a first DVR plate 114 that has a head 106, a neck 108 and a shaft 110 that extends along a longitudinal axis 101.

Head 106 includes a plurality of locking apertures 250, each of which is assembled with a first drill guide 330. Each of locking apertures 250 of head 106 defines a desired, fixed trajectory, such that insertion of first fastener 401 into each locking aperture 250 of head 106 provides subchondral support of the articulation surface of the wrist joint of the distal radius.

Shaft 110 includes a plurality of locking apertures 250, a plurality of non-locking apertures 270, and one UR slot 310, wherein the respective axis of each aperture is generally directed inwardly towards the center of the underlying bone. Each of locking apertures 250 is assembled with one of first drill guides 330. Each of locking apertures 250, non-locking apertures 270, and UR slot 310 is sized for receiving first fastener 401. Each locking aperture 250 of shaft 110 is paired closely together with one of the non-locking apertures 270 to form four, spaced-apart, groupings or clusters, including a first grouping 120, a second grouping 130, a third grouping 140 and a fourth grouping 146, and corresponding to a first region 121, a second region 131, a third region 141, and a fourth region 147 on shaft 110. First grouping 120 opposes second grouping 130 about longitudinal axis 111 of plate 104, such that aperture axes 123 and 125 of first grouping 120 cross-over aperture axes 133 and 135 of second grouping 130. Similarly, third grouping 140 opposes fourth grouping 146.

During the surgical procedure, the surgeon may insert one of first fasteners 401 into each of regions 121, 131, 141, and 147. The surgeon may choose whether to select one of locking apertures 250 or one of non-locking apertures 270 for each region. In general, surgeons may choose to use locking apertures 250 if the underlying bone is not in condition to provide optimal engagement with the threads of shaft 110 of first fastener 401.

It should be appreciated that first DVR assembly 102 may be attached to the distal radius of a patient using only one type of bone fastener, i.e., a plurality of first fasteners 401 of varying lengths. In many current bone plate systems for fixation of the distal radius, a number of different types of fasteners are required. By using only one type, it is possible to reduce the number of instruments required in DVR kit 100, thereby reducing the size of container 10 (FIG. 4) and potentially lowering the overall cost of DVR kit 100. Using only one type of fastener also may help surgeons, especially those who are not greatly experienced doing the procedure, to perform the surgical procedure more quickly and without using the fasteners inappropriately.

Figure 52:
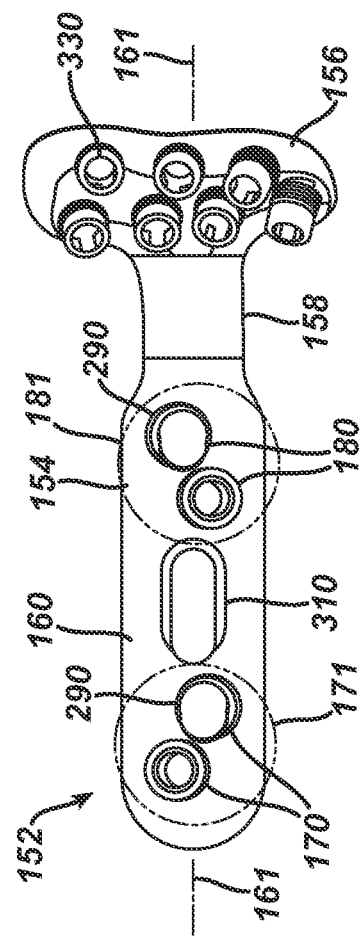
FIG. 52 is a top view of the second DVR assembly of FIG. 51.
Figure 51:
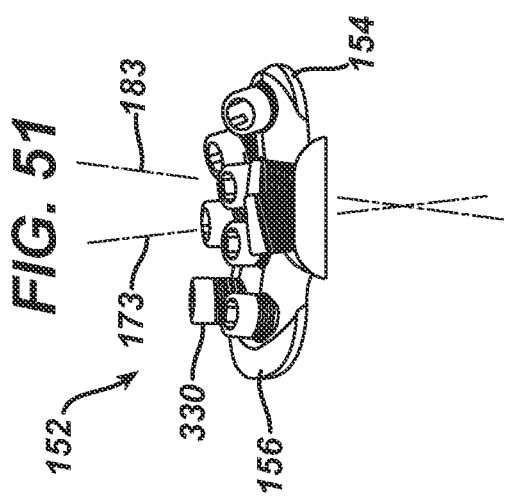
FIG. 51 is an end view of a second DVR assembly.
Figure 53:
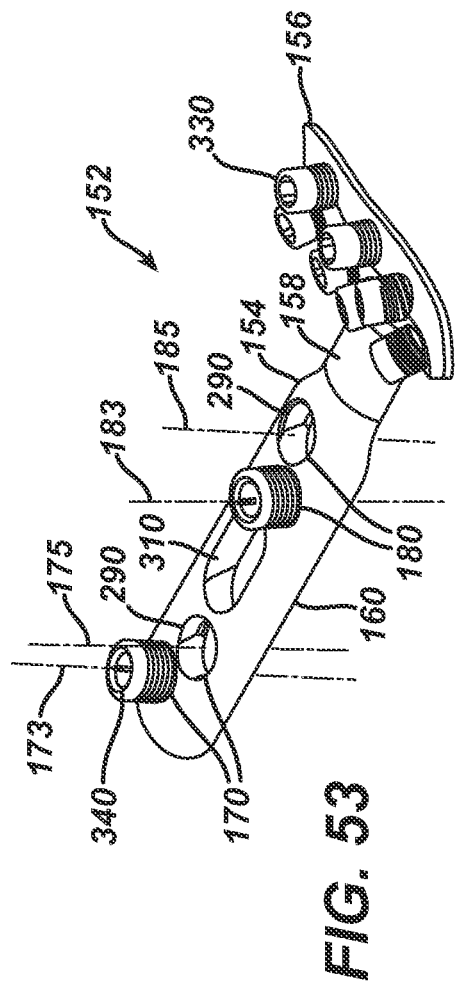
FIG. 53 is a perspective view of the second DVR assembly of FIG. 51.

FIG. 51 is an end view, FIG. 52 is a top view, and FIG. 53 is a perspective view of a second DVR assembly 152, which includes a second DVR plate 154 assembled with a plurality of first drill guides 330, and a plurality of second drill guides 340. Second DVR plate has a head 156, a neck 158 and a shaft 160 that extends along a longitudinal axis 161.

Head 156 includes a plurality of locking apertures 250, each of which is assembled with one of first drill guides 330 and is sized for receiving one of first fasteners 401. Each of locking apertures 250 of head 156 defines a desired, fixed trajectory, such that insertion of first fastener 401 into each locking aperture 250 of head 156 provides subchondral support of the articulation surface of the wrist joint of the distal radius.

Shaft 154 includes two of locking apertures 250, each of which is assembled with one of second drill guides 340 and is sized to receive one of second fasteners 451. Each of locking apertures 250 in shaft 154 is paired closely together with one of UR apertures 290, each of which is sized to receive one of second fasteners 451, to form a first grouping 170 that is spaced apart from a second grouping 180 along axis 161. First grouping 170 corresponds to a first region 171 and second grouping 180 corresponds to a second region 181 of plate 154. As for first DVR assembly 102, the axes 173, 175, 183 and 185 of the apertures of shaft 160 of second DVR assembly 152 are generally directed towards the center of the bone. Shaft 154 also includes BR slot 320 positioned approximately midway along axis 161.

Second DVR assembly 152 requires two types of fasteners, i.e., first fasteners 401 and second fasteners 451 of varying lengths. However, we envision that using two of second fasteners 451 in shaft 160 precludes the need to use four of first fasteners 401 in shaft 110 of first DVR assembly 102. This facilitates a quicker surgical procedure and eliminates the cost of the additional two fasteners.

Another feature of second DVR assembly 152 is the enhanced ability to draw the fractured bone fragments together axially as the fasteners are inserted. That is because, the dynamic compression that is achievable using UR apertures 290, if done in proper sequence, may be additive to the dynamic compression that is achievable using UR slot 310.

FIG. 54 is an end view, FIG. 55 is a top view, and FIG. 56 is a perspective view of a third DVR assembly 552, which includes a third DVR plate 554 assembled with a plurality of first drill guides 330, and a plurality of second drill guides 340. Third DVR plate 554 has a head 556, a neck 558 and a shaft 560 that extends along a longitudinal axis 561.

Head 556 includes a plurality of locking apertures 250, each of which is assembled with one of first drill guides 330 and is sized for receiving one of first fasteners 401. Each of locking apertures 250 of head 556 defines a desired, fixed trajectory, such that insertion of first fastener 401 into each locking aperture 250 of head 556 provides subchondral support of the articulation surface of the wrist joint of the distal radius.

Shaft 554 includes two of locking apertures 250, each of which is assembled with one of second drill guides 340 and is sized to receive one of second fasteners 451. Each of locking apertures 250 in shaft 554 is paired closely together with one of BR apertures 320, each of which is sized to receive one of second fasteners 451, to form a first grouping 570 that is spaced apart from a second grouping 580 along axis 561. First grouping 570 corresponds to a first region 571 and second grouping 180 corresponds to a second region 581 of plate 554. As for the previously described DVR assemblies 102 and 152, the axes of the apertures of shaft 560 of third DVR assembly 552 are generally directed towards the center of the bone. Shaft 554 also includes BR slot 320 positioned approximately midway along axis 561.

Third DVR assembly 552 requires two types of fasteners, i.e., first fasteners 401 and second fasteners 451 of varying lengths. However, as for second DVR assembly 152, we envision that using two of second fasteners 551 in shaft 560 precludes the need to use four of first fasteners 401 in shaft 110 of first DVR assembly 102. This facilitates a quicker surgical procedure and eliminates the cost of the additional two fasteners.

Again as with second DVR assembly 152, third DVR assembly 552 has the enhanced ability to draw the fractured bone fragments together axially as the fasteners are inserted since the dynamic compression that is achievable using BR apertures 501, if done in proper sequence, may be additive to the dynamic compression that is achievable using BR slot 320. However, third DVR assembly 552 has the additional ability to provide dynamic compression in either direction along axis 561 of plate 554.

We have shown and described various embodiments and examples. However, a person having ordinary skill in the art may modify the methods and devices described herein without departing from the overall concept. For instance, the specific materials, dimensions and the scale of drawings should be understood to be non-limiting examples. Accordingly, we do not intend the scope of the following claims to be understood as limited to the details of structure, materials or acts shown and described in the specification and drawings.

The invention claimed is:

1. A disposable single indication orthopedic trauma surgical kit, comprising:
a sterile sealed container;
no bone plates other than a single bone plate precontoured and sized to match an anatomic shape of a portion of a bone of a patient's extremity, the single bone plate comprising a plurality of fastener apertures;
a plurality of fasteners, each comprising a head and a shaft, the heads of all of the fasteners being the same size and being dimensioned to mate with the fastener apertures, the plurality of fasteners being the only fasteners disposed in the sterile sealed container; and
a disposable torque driver adapted to engage the fastener heads; and drill guides;
wherein the single bone plate, the plurality of fasteners, the disposable torque driver, and the drill guides are contained in the sterile sealed container; and
wherein the sterile sealed container includes an integrally formed reservoir and an integrally formed stripping slot, the stripping slot being configured to remove the drill guides from the torque driver, the reservoir being configured to collect the drill guides removed from the torque driver by the stripping slot in a visible linear arrangement.

2. The surgical kit of claim 1, wherein the portion of the bone is selected from the group consisting of the right distal volar radius, the left distal volar radius, the right fibula, the left fibula, the right proximal radius, the left proximal radius, the right navicular, the left navicular, the right distal ulna, and the left distal ulna.

3. The surgical kit of claim 1, wherein each of the plurality of fastener apertures of the single bone plate dimensioned to receive the same sized head of the plurality of fasteners.

4. The surgical kit of claim 1, further comprising a wire drill and a depth gage, all contained in the sterile sealed container.

5. The surgical kit of claim 1, wherein the plurality of fasteners comprises 36 or fewer fasteners.

6. The surgical kit of claim 5, wherein all of the fasteners in the surgical kit have only one of nine or fewer different shaft lengths.

7. The surgical kit of claim 1, wherein the plurality of fasteners are arranged in the sterile sealed container in a plurality of groupings of four or fewer of the fasteners, the four or fewer fasteners in a respective grouping having the same shaft length.

8. The surgical kit of claim 7, wherein the sterile sealed container includes labels to indicate the shaft length of each of the plurality of groupings of fasteners.

9. The surgical kit of claim 1, wherein the container includes a plurality of fastener length gages to aid a user in determining a length of each of the plurality of fasteners.

10. The surgical kit of claim 1, wherein the kit is resterilizable by a steam autoclave once the sterile sealed container has been opened.

11. An orthopedic surgical kit, comprising:
a bone plate precontoured and sized to match an anatomic shape of a portion of a bone of a patient's extremity, the bone plate comprising a plurality of fastener apertures;
a plurality of drill guides;
a plurality of fasteners, each comprising a head and a shaft, the heads being dimensioned to mate with the fastener apertures;
a torque driver adapted to engage the fastener heads; and
a sterile sealed container;
wherein the bone plate, the plurality of drill guides, the plurality of fasteners and the torque driver are contained in the sterile sealed container,
wherein the plurality of fasteners are arranged in the container in a plurality of groupings of the fasteners, a first one of the plurality of groupings including only fasteners having a first shaft length, a second one of the plurality of groupings including only fasteners having a second shaft length that is different from the first shaft length, the fasteners in the first one of the plurality of groupings being segregated from the fasteners in the second one of the plurality of groupings, and
wherein the container includes an integrally formed reservoir and an integrally formed stripping slot, the stripping slot being configured to remove the drill guides from the torque driver, the reservoir being configured to collect the drill guides removed from the torque driver by the stripping slot in a visible linear arrangement.

12. The surgical kit of claim 11, wherein the container includes a plurality of fastener length gages to aid a user in determining the shaft length of each of the plurality of fasteners.

13. A disposable single indication orthopedic trauma surgical kit comprising:
a) a single bone plate precontoured and sized to match an anatomic shape of a portion of a bone of a patient's extremity, the single bone plate comprising a plurality of fastener holes;
b) a plurality of fasteners, each comprising a head and a shaft, the heads being adapted to interface with the fastener holes;
c) a disposable torque driver adapted to engage the fastener heads;
d) one or more wire drills;
e) a plurality of drill guides;
f) a disposable depth gage; and
g) a sterile sealed container;
wherein the single bone plate, the plurality of fasteners, the disposable torque driver, the one or more wire drills, the plurality of drill guides, and the disposable depth gage are contained in the sterile sealed container,
wherein the plurality of fasteners are arranged in the container in a plurality of groupings of the fasteners, a first one of the plurality of groupings including only fasteners having a first shaft length, a second one of the plurality of groupings including only fasteners having a second shaft length that is different from the first shaft length, the fasteners in the first one of the plurality of groupings being segregated from the fasteners in the second one of the plurality of groupings,
wherein each of the plurality of fasteners has the same sized head, and the plurality of fasteners are the only fasteners disposed within the sterile sealed container; and
wherein the container includes an integrally formed reservoir and an integrally formed stripping slot, the stripping slot being configured to remove the drill guides from the torque driver, the reservoir being configured to collect the drill guides removed from the torque driver by the stripping slot in a visible linear arrangement.

14. The surgical kit of claim 13, wherein each of the plurality of fastener holes of the single bone plate is dimensioned to receive the same sized head of the plurality of fasteners.

15. The surgical kit of claim 13, wherein the container includes labels to indicate the shaft length of the fasteners in each of the plurality of groupings of the fasteners.

16. The surgical kit of claim 13, wherein the container includes a plurality of fastener length gages to aid a user in determining the shaft length of each of the plurality of fasteners.

* * * * *